United States Patent
Alley et al.

(10) Patent No.: US 9,889,146 B2
(45) Date of Patent: Feb. 13, 2018

(54) BENZOXABOROLE COMPOUNDS AND USES THEREOF

(71) Applicants: Anacor Pharmaceuticals, Inc., Palo Alto, CA (US); GlaxoSmithKline LLC, Philadelphia, PA (US)

(72) Inventors: Michael Richard Kevin Alley, Santa Clara, CA (US); Katherine Widdowson, King of Prussia, PA (US)

(73) Assignee: Anacor Pharmaceuticals, Inc., Palo Alto, CA (US)

( * ) Notice: Subject to any disclaimer, the term of this patent is extended or adjusted under 35 U.S.C. 154(b) by 0 days.

(21) Appl. No.: 15/162,125

(22) Filed: May 23, 2016

(65) Prior Publication Data

US 2017/0071961 A1 Mar. 16, 2017

Related U.S. Application Data

(63) Continuation of application No. 14/394,427, filed as application No. PCT/US2013/032014 on Mar. 15, 2013, now abandoned.

(60) Provisional application No. 61/624,294, filed on Apr. 14, 2012.

(51) Int. Cl.
*A61K 31/69* (2006.01)
*A61K 31/195* (2006.01)
*A61K 31/198* (2006.01)

(52) U.S. Cl.
CPC ............ *A61K 31/69* (2013.01); *A61K 31/198* (2013.01)

(58) Field of Classification Search
CPC .............................. A61K 31/69; A61K 31/198
USPC ..................................... 514/64, 561
See application file for complete search history.

(56) References Cited

U.S. PATENT DOCUMENTS

| 2004/0203094 A1 | 10/2004 | Martinis |
| 2007/0155699 A1 | 7/2007 | Baker |
| 2009/0227541 A1 | 9/2009 | Baker |

*Primary Examiner* — Shengjun Wang
(74) *Attorney, Agent, or Firm* — Morgan, Lewis & Bockius LLP

(57) ABSTRACT

Norvaline and/or other amino acids that are capable of being acylated onto tRNA$^{Leu}$ by LeuRS, in combination with substituted benzoxaboroles, such as a compound having a structure according to formula III:

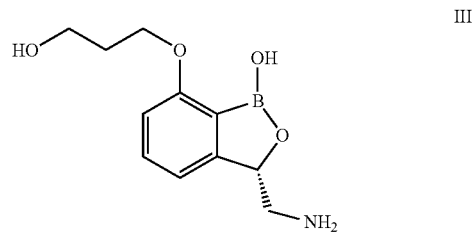

and methods for decreasing the frequency of resistance and/or reducing the rate of resistance and/or suppressing the emergence of resistance that develops in bacteria exposed to a substituted benzoxaborole or salt thereof by administering a combination of a substituted benzoxaborole such as a compound of formula III or salt thereof and an amino acid or a salt thereof.

7 Claims, 1 Drawing Sheet

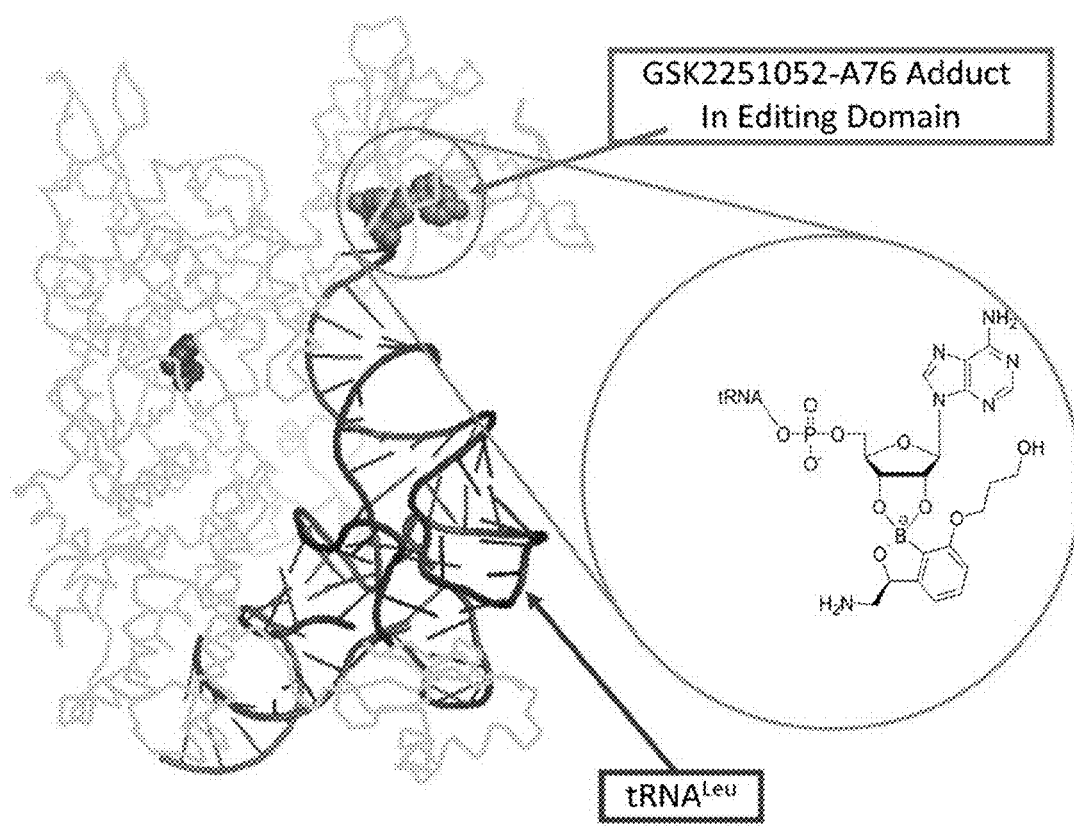

SEQUENCE LISTING

```
<160> NUMBER OF SEQ ID NOS: 1

<210> SEQ ID NO 1
<211> LENGTH: 31
<212> TYPE: PRT
<213> ORGANISM: Artificial Sequence
<220> FEATURE:
<223> OTHER INFORMATION: E.coli

<400> SEQUENCE: 1

Thr Thr Arg Pro Asp Thr Phe Met Gly Cys Thr Tyr Leu Ala Val Gly
1               5                   10                  15

Thr Gly Ala Val Met Ala Val Pro Gly His Asp Gln Arg Asp Tyr
            20                  25                  30
```

BENZOXABOROLE COMPOUNDS AND USES THEREOF

CROSS REFERENCE TO RELATED APPLICATIONS

This application is a continuation of U.S. patent application Ser. No. 14/394,427 filed Oct. 14, 2014, which is a 371 U.S. National Phase Application of International Patent Cooperation Treaty Application PCT/US13/32014 filed Mar. 15, 2013, which claims priority from U.S. Provisional Application No. 61/624,294 filed Apr. 14, 2012, the contents of which are hereby incorporated by reference herein in their entirety.

GOVERNMENT LICENSE RIGHTS

This invention was made with US Government support under HHSO100201100016C awarded by BARDA. The US Government has certain rights in the invention.

FIELD OF THE INVENTION

The present invention relates to the use of a novel class of boron-containing molecules which bind to the editing domain of leucyl-tRNA synthetase (LeuRS), and more particularly relates to such novel class of boron-containing molecules in combination with amino acids and/or amino acid salts for treatment of bacterial infections in animal subjects.

BACKGROUND ART

The global rise of bacteria and other microorganisms resistant to antibiotics and antimicrobials in general, poses a major threat. Deployment of massive quantities of antimicrobial agents into the ecosphere during the past 60 years has introduced a powerful selective pressure for the emergence and spread of antimicrobial-resistant pathogens. Thus, there is a need to discover new broad spectrum antimicrobials, such as antibiotics, useful in combating microorganisms, especially those with multidrug-resistance.

Boron-containing molecules such as benzoxaboroles that are useful as antimicrobials have been described previously, see e.g. "Benzoxaboroles—Old compounds with new applications" Adamczyk-Woźniak, A. et al., *Journal of Organometallic Chemistry* Volume 694, Issue 22, 15 Oct. 2009, Pages 3533-3541, and U.S. Pat. Pubs. US20060234981 and US20070155699. Generally speaking, a benzoxaborole has the following structure and substituent numbering system:

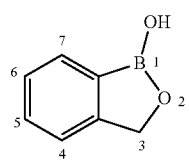

I

Certain benzoxaboroles which are monosubstituted at the 3-, 6-, or 7-position, or disubstituted at the 3-/6- or 3-/7- positions are surprisingly effective antibacterials, and they have been found to bind to the editing domain of LeuRS in association with tRNA$^{Leu}$. Such compounds have been described in U.S. Pat. No. 7,816,344. Using combinations of certain substituted benzoxaboroles with norvaline and/or other amino acid analogs and their salts to: (a) reduce the rate of resistance that develops; and/or (b) decrease the frequency of resistance that develops; and/or (c) suppress the emergence of resistance, in bacteria exposed to compounds of formulas I and II, is described herein.

SUMMARY OF THE INVENTION

Embodiments of the present invention feature combinations of norvaline and/or other amino acids with certain substituted benzoxaboroles, such as those described in U.S. Pat. No. 7,816,344 (the contents of which are hereby incorporated by reference herein in their entirety) for use in the treatment of bacterial infections in animal subjects. In particular embodiments, such benzoxaboroles are used, in combination with an amino acid or amino acid salt, to decrease the rate of resistance to such substituted benzoxaboroles, in an animal subject with a bacterial infection, particularly in an animal subject with a Gram negative (−) bacterial infection.

In particular embodiments, the substituted benzoxaborole is a compound having a structure according to formula II:

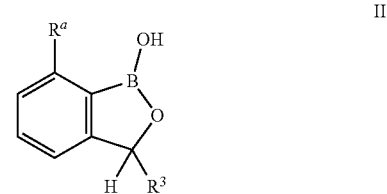

II wherein $R^3$ is a member selected from H, cyano, substituted or unsubstituted nitroalkyl and substituted or unsubstituted aminoalkyl; $R^a$ is a member selected from H and —YR$^5$ wherein Y is a member selected from O and S; $R^5$ is a member selected from H, substituted or unsubstituted alkyl and substituted or unsubstituted heteroalkyl with the proviso that $R^a$ and $R^3$ cannot both be H; and with the proviso that when $R^3$ is H, $R^a$ does not have a structure which is a member selected from: unsubstituted benzyloxy, —OCH$_2$COOH, methoxy, ethoxy, with the proviso that when $R^a$ is H, $R^3$ is not cyano, or a salt thereof.

More particularly, substituted benzoxaboroles of formula II, in combination with an amino acid or amino acid salt that is capable of being acylated onto tRNA$^{Leu}$ by LeuRS, decrease the frequency of resistance and/or reduce the rate of resistance and/or suppress the emergence of resistance, that develops in bacteria exposed to said substituted benzoxaboroles, in an animal subject with a bacterial infection, by co-administration, or more particularly sequential administration, or more particularly simultaneous administration of the substituted benzoxaborole with an amino acid or its salt to the animal subject with the bacterial infection.

More particularly, one embodiment of the invention provides a method for decreasing the frequency of resistance and/or reducing the rate of resistance and/or suppressing the emergence of resistance that develops in bacteria exposed to a substituted benzoxaborole or salt thereof, comprising administering to a subject having a bacterial infection a combination of a substituted benzoxaborole of formula II or salt thereof and an amino acid or a salt thereof, wherein the decreasing the rate and/or reducing the rate and/or suppressing the emergence of resistance in the subject is assessed relative to the frequency, rate or emergence of resistance that develops in a subject administered the substituted benzoxaborole or salt thereof in the absence of the amino acid or salt thereof. In another particular embodiment there is provided a method for decreasing the frequency of resistance and/or reducing the rate of resistance and/or suppressing the emergence of resistance that develops in bacteria exposed to a substituted benzoxaborole, comprising administering to a subject having a bacterial infection a substituted benzoxaborole of formula II or a salt thereof and an amino acid or a salt thereof.

In a particular embodiment, the substituted benzoxaborole is a compound of formula III,

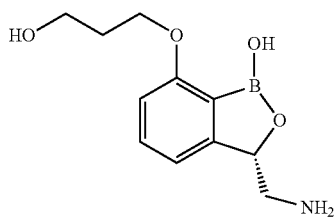

III and the amino acid or its salt is allyl glycine, norvaline, methionine, norleucine, isoleucine, homocysteine, homoserine or valine. In more particular embodiments, the amino acid or its salt may be a structural analog of allylglycine, norvaline, methionine, norleucine, isoleucine, homocysteine, homoserine, valine that is capable of being acylated onto tRNA$^{Leu}$ by LeuRS.

In more particular embodiments, the substituted benzoxaborole is a compound of formula III and the amino acid or its salt is norvaline or a structural analog of norvaline.

In more particular embodiments, the substituted benzoxaborole is a compound of as indicated below

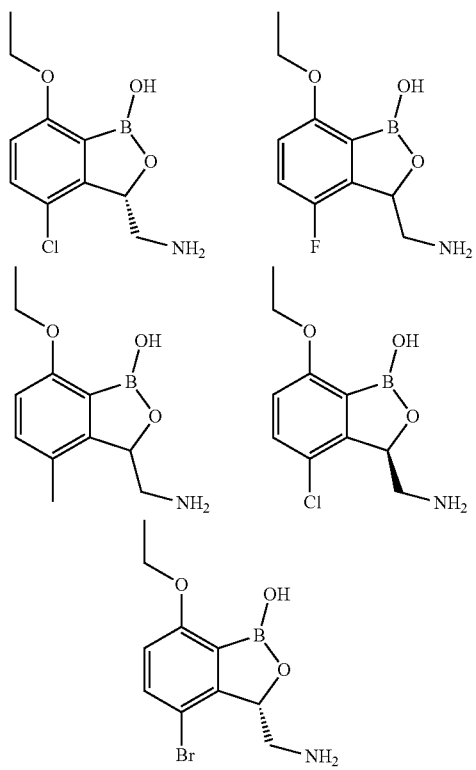

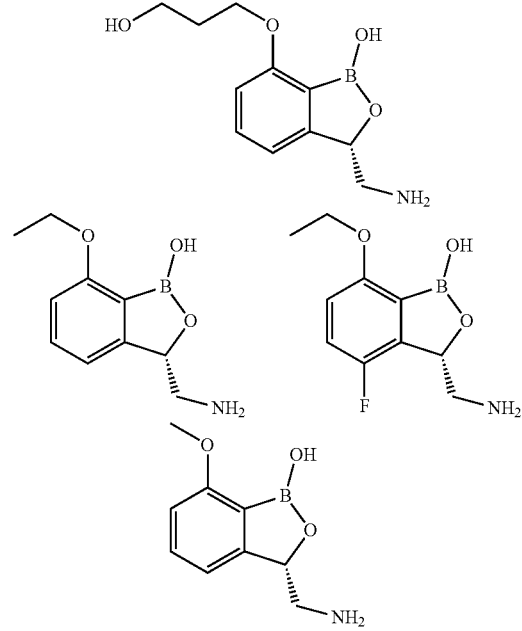

and the amino acid or its salt is norvaline or a structural analog of norvaline.

A structural analog of norvaline is an amino acid or amino acid analog which has a similar chemical structure and/or a similar 3-dimensional geometry and/or a similar electronic geometry and/or similar physico/chemico properties to norvaline, and/or is capable of being aminoacylated onto a bacterial tRNA$^{Leu}$ by bacterial LeuRS. Administration may be by i.v., oral, suppository, or any other route of administration known by one of skill in the art for delivering small molecules, including such methods described in U.S. Pat. No. 7,816,344 for administration of the substituted benzoxaborole compounds described therein. Similarly, formulations may include any known to those of skill in the art, including those formulations described in U.S. Pat. No. 7,816,344 for the substituted benzoxaborole compounds described therein.

As described herein, embodiments of the invention include coadministering, whether simultaneously, sequentially or in combination, a substituted benzoxaborole or salt thereof, preferably a substituted benzoxaborole of formula II, with an amino acid or amino acid salt that is capable of being aminoacylated onto tRNA$^{Leu}$ by LeuRS, to a subject having a bacterial infection. More preferably, the benzoxaborole is the compound of formula III or a salt thereof, and the amino acid or amino acid salt, or structural analog thereof, is norvaline. In certain embodiments, the bacterial infection is caused by bacteria that is multi-drug resistant. In certain embodiments, the bacterial infection is a Gram negative (−) bacterial infection.

In other particular embodiments there is provided a method for killing bacterial cells comprising contacting the bacterial cells or a subject suffering from a bacterial infection with a compound of formula III or a salt thereof and norvaline or salt thereof or a structural analog of norvaline capable of being aminoacylated onto bacterial tRNA$^{Leu}$ by bacterial LeuRS, such that contacting kills bacterial cells. In another embodiment there is provided a method of suppressing the emergence of a resistant mutant in a bacteria contacted with the substituted benzoxaborole according to either of formulas II or III in a subject with a bacterial infection, the method comprising coadministering, whether simultaneously, sequentially or in combination, the substituted benzoxaborole according to either of formulas II or III or a salt thereof with an amino acid or salt thereof which is capable of being aminoacylated by bacterial LeuRS onto bacterial tRNA$^{Leu}$ such that coadministering suppresses the emergence of a resistant mutant in bacteria cultured from the bacterial infection of the subject. In particular embodiments, the substituted benzoxaborole is a compound of formula III or a salt thereof and the amino acid is norvaline or a salt thereof. In other particular embodiments, the resistant mutant in the bacteria cultured from the bacterial infection of the patient is evidenced by a mutation in the editing domain of bacterial LeuRS.

BRIEF DESCRIPTIONS OF THE DRAWINGS

FIG. 1 is a three-dimensional depiction of GSK2251052 bound to A76 of the editing domain of bacterial LeuRS.

Table 1 is a table showing MIC values for GSK2251052 against a multitude of bacterial strains.

Table. 2a shows GSK2251052 in vitro activity against *Pseudomonas aeruginosa* compared to other known antibiotic agents. (GSK2251052 percent susceptible based on potential susceptible breakpoint of ≤4 µg/mL)

Table 2b summarizes frequency of resistance information for GSK2251052.

Table 3 shows pre-clinical in vitro frequency of resistance of three bacterial species to GSK2251052 vs standard comparator antibiotics.

Table 4 shows MIC values determined for *E. coli* ATCC 25922 wild type and resistant mutants to GSK2251052 and mutations found in the editing domain of LeuRS.

Table 5 shows MIC values determined for *P. aeruginosa* ATCC27853 wild type and resistant mutants to GSK2251052 and mutations found in the editing domain of LeuRS.

Table 6 MIC values determined for *K. pneumoniae* ATCC13883 wild type and resistant mutants to GSK2251052 and mutations found in the editing domain of LeuRS.

Table 7 is a summary of the MIC values (µg/mL) determined for *E. coli*, *P. aeruginosa* and *K. pneumoniae* wild type and mutant strains.

Table 8 shows *E. coli* ATCC 25922, *K. pneumoniaev* ATCC 13883, *P. aeruginosa* ATCC 27853 wild type and mutants MICs to GSK2251052, norvaline, and norleucine in minimal media.

Table 9 shows MIC values determined for *E. coli* ATCC 25922 wild type and mutants to common antibiotics.

Table 10 shows MIC values determined for *K. pneumoniae* ATCC 13883 wild type and mutants to common antibiotics.

Table 11 shows MIC values determined for *P. aeruginosa* ATCC 27853 wild type and mutants to common antibiotics.

Table 12 shows MIC values determined for a first *E. coli* clinical isolate, the mutation change, and increased susceptibility to norvaline.

Table 13 shows MIC values showing sensitivity of *Escherichia coli* 1161435 parent strain and mutant strains B4, B26 and B35 to leucine analogs in Mueller Hinton (MH) and M9 minimal media (M9).

Table 14 shows MIC values determined for a second *E. coli* clinical isolate, follow-up determinations at days 6 and 11, and the mutation changes identified.

Table 15 shows subject Identification number and source of bacterial strains for clinical isolates used in the present application.

Table 16 shows Minimal Inhibitory Concentration (MIC) values for GSK2251052 and Norvaline in M9 minimal media against *E. coli* isolates from subject *E. coli* 1.

Table 17 shows the effect of norvaline in the frequency of spontaneous resistance to GSK2251052 at 4 µg/mL for two *E. coli* strains grown in minimal Media or in rich media.

The foregoing features of the invention will be more readily understood by reference to the following detailed description, taken with reference to the accompanying drawings, in which:

DETAILED DESCRIPTION OF SPECIFIC EMBODIMENTS

"Amino Acid," as used herein refers to the genus encompassing hydrophilic amino acids, acidic amino acids, basic amino acids, polar amino acids, hydrophobic amino acids, aromatic amino acids, non-polar amino acids and aliphatic amino acids, including the genus and the species therein. Amino acids also encompass amino-carboxylic acid species other than α-amino acids, e.g., aminobutyric acid (aba), aminohexanoic acid (aha), aminomethylbenzoic acid (amb) etc.

"Combination of the invention," as used herein refers to the combinations discussed herein, salts (e.g. pharmaceutically acceptable salts), prodrugs, solvates and hydrates of these compounds.

I. Introduction

Ia. Aminoacyl-tRNA Synthetases (AARS)

Aminoacyl-tRNA synthetases (AARS) are a family of enzymes required for protein synthesis that have been under-utilized as targets for antimicrobials. Aminoacyl-tRNA synthetases catalyze aminoacylation of tRNAs by joining an amino acid to its cognate tRNA. One such AARS that is essential for protein synthesis in bacteria is Leucyl-tRNA synthetase (LeuRS).

LeuRS is an essential enzyme for protein synthesis. Inhibition of LeuRS prevents protein synthesis and stops the growth of bacteria. LeuRS has a catalytic domain for attaching leucine onto the tRNA via aminoacylation to form Leu-tRNA$^{LEU}$; and the editing domain, which "proof-reads" the charged tRNA$^{LEU}$ to ensure that the correct amino acid has been attached.

LeuRS attaches leucine to the 3' terminal nucleotide (adenosine) of tRNA$^{Leu}$ (A76). The two active sites in LeuRS are separated by 38 Å. As stated above, the catalytic domain is where aminoacylation of tRNA$^{Leu}$ occurs and the editing domain is where proof-reading occurs, and where LeuRS hydrolyzes the incorrect amino acid from any mischarged tRNA$^{LEU}$. A76 moves between the two active sites, and the editing domain ensures fidelity of protein synthesis. LeuRS can charge (aminoacylate) tRNA$^{LEU}$ with amino acids other than leucine, including isoleucine, valine, methionine, and norvaline. In wild type LeuRS, the editing domain hydrolyzes amino acids from aminoacyl-tRNA$^{Leu}$ that have been charged with any amino acid other than leucine. Mischarged tRNA$^{Leu}$ are deleterious to the cell.

Ib. GSK2251052 Antibacterial Activity

The compound of formula III and its salts, also referred to herein as GSK2251052 or (S)-3-aminomethyl-7-(3-hydroxy-propoxy)-3h-benzo[c][1,2]oxaborol-1-ol is a 7-substituted benzoxaborole as shown below

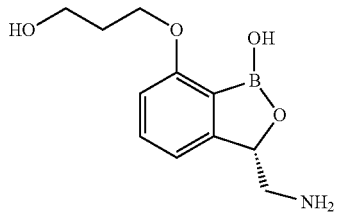

III that forms an adduct with the tRNA$^{Leu}$ in the editing domain of LeuRS, locking LeuRS in an unproductive state (see FIG. 1).

GSK2251052 was tested for antibacterial activity against a wide variety of pathogens, as shown in Table 1, including Enterobacteriaceae, and several multidrug resistant pathogen strains. Moreover, the MIC90 values ranged from 0.5 to 2 µg/mL for all bacterial strains tested.

TABLE 1

| Organism (Selected Phenotypes) | No. of Isolates | MIC$_{90}$(µg/mL) | | | | |
|---|---|---|---|---|---|---|
| | | GSK2251052 | Tigecycline | Imipenem | Cefepime | Levofloxacin |
| Enterobacteriaceae | 2029 | *1 | *2 | **2 | *4 | ***16 |
| E. coli (WT) | 214 | *1 | *0.25 | *0.25 | *≤1 | ***16 |
| E. coli (ESBL) | 27 | *1 | *0.5 | *0.5 | ***>32 | ***>16 |
| Klebsiella spp. (WT) | 159 | *1 | *1 | *0.25 | *≤1 | **4 |
| Klebsiella spp. (ESBL) | 71 | *1 | *2 | *0.5 | ***>32 | ***>16 |
| Klebsiella spp. (KPC) | 26 | *2 | *2 | ***64 | ***>32 | ***>16 |
| Enterobacter aerogenes (WT) | 199 | *1 | *0.5 | **2 | *≤1 | *≤0.5 |
| Enterobacter aerogenes (AmpC) | 51 | *1 | *2 | **2 | *8 | ***16 |
| Enterobacter cloacae (WT) | 202 | *1 | *0.5 | *1 | *≤1 | *≤0.5 |
| Enterobacter cloacae (AmpC) | 50 | *0.5 | **4 | *1 | ***>32 | ***16 |
| Citrobacter freundii (AmpC) | 60 | *1 | *2 | *1 | **16 | ***8 |
| Morganella morganii (AmpC) | 18 | *2 | **4 | ***4 | ***>32 | ***>16 |
| Proteus mirabilis (WT) | 235 | *1 | **4 | ***4 | *≤1 | ***8 |
| Proteus vulgaris (WT) | 41 | *1 | *2 | ***4 | *≤1 | *≤5 |
| Providencia spp.(all) | 68 | *1 | **4 | **2 | ***>32 | ***>16 |
| S. marcescens (AmpC) | 26 | *1 | *2 | **2 | *8 | **4 |

| Organism (Selected Phenotypes) | MIC$_{90}$(µg/mL) | | | | | |
|---|---|---|---|---|---|---|
| | Gentamicin | Ceftazidime | Polymixin B | Piperacillin/ Tazobactam | Amoxicillin/ Clavulanate | Ampicillin |
| Enterobacteriaceae | ***16 | ***>16 | ***>8 | **64 | ***>64 | ***>64 |
| E. coli (WT) | ***>16 | *≤1 | *1 | *8 | **16 | ***>64 |
| E. coli (ESBL) | ***>16 | ***>16 | *2 | ***>128 | ***64 | ***>64 |
| Klebsiella spp. (WT) | *1 | *≤1 | *1 | *16 | *8 | ***>64 |
| Klebsiella spp. (ESBL) | ***>16 | ***>16 | *2 | ***>128 | ***32 | ***>64 |
| Klebsiella spp. (KPC) | ***16 | ***>16 | ***>8 | ***>128 | ***>64 | ***>64 |
| Enterobacter aerogenes (WT) | *1 | *≤1 | **4 | *8 | ***>64 | ***>64 |
| Enterobacter aerogenes (AmpC) | *4 | ***>16 | *2 | ***128 | ***>64 | ***>64 |
| Enterobacter cloacae (WT) | *1 | *≤1 | ***>8 | *4 | ***>64 | ***>64 |
| Enterobacter cloacae (AmpC) | ***>16 | ***>16 | **4 | ***>128 | ***>64 | ***>64 |
| Citrobacter freundii (AmpC) | ***>16 | ***>16 | *1 | ***>128 | ***>64 | ***>64 |
| Morganella morganii (AmpC) | ***>16 | ***>16 | ***>8 | **64 | ***>64 | ***>64 |
| Proteus mirabilis (WT) | *4 | *≤1 | ***>8 | *1 | *8 | ***>64 |
| Proteus vulgaris (WT) | *2 | *≤1 | ***>8 | *1 | *8 | ***>64 |
| Providencia spp.(all) | ***>16 | **8 | ***8 | *8 | ***>64 | ***>64 |
| S. marcescens (AmpC) | ***>16 | ***>16 | ***>8 | **32 | ***>64 | ***>64 |

Key:
*** = resistant;
** = intermediate;
* = susceptible based on CLSI interpretive criteria (M100-S21, 2011), except for GSK2251052 (susceptible defined as MICs ≤4 µg/mL), tigecycline (FDA interpretive criteria used to define susceptibility) and polymixinB (susceptible ≤2 µg/mL, intermediate 4 µg/mL, resistant ≥8 µg/mL)

GSK2251052 was tested for activity against *P. aeruginosa*, and its activity was compared to other antibiotics of known activity. The results are shown below in Tables 2a and 2b. Of 2,008 clinical isolates tested (from 2009-2010 subjects, of which 40% were from North America) greater than 90% were susceptible to GSK2251052 based on a potential susceptible breakpoint of ≤4 μg/mL.

TABLE 2a

GSK2251052 in vitro activity: *P. aeruginosa* ((GSK2251052 percent susceptible based on potential susceptible breakpoint of ≤4 μg/mL)

| Antibiotic | % susceptible |
|---|---|
| GSK2250152 | 92.8 |
| Amikacin | 90.2 |
| Pip/tazo | 81.3 |
| Meropenem | 79.3 |
| Cefepime | 75.3 |
| Imipenem | 72.9 |
| Ticar/clav | 67.6 |
| Ceftazidime | 66.4 |
| Levofloxacin | 63.7 |
| Colistin | 62.3 |

TABLE 2b

| Compound | MIC (μg/mL) | | |
|---|---|---|---|
| | Range | 50% | 90% |
| GSK2251052 | 0.06-64 | 2 | 4 |

When GSK2251052 binds to the LeuRS editing domain, the boron atom in the benzoxaborole ring bonds to the cis-diols of the terminal ribonucleotide of tRNA$^{Leu}$ forming an adduct that traps the 3"-end of tRNA$^{Leu}$ in the editing domain, thereby preventing its translocation to the catalytic domain. This blocks tRNA$^{Leu}$ from being aminoacylated, which ultimately leads to the inhibition of protein synthesis. In certain situations, the editing domain of the LeuRS enzyme is mutated in such a way that it no longer binds a substituted benzoxaborole, for example GSK2251052 and similar analogs. Such a mutated LeuRS enzyme is capable of protein synthesis. However, it can no longer edit mischarged amino acids.

II. Combinations

In an exemplary embodiment, the invention provides a) a substituted benzoxaborole or salt thereof as described in U.S. Pat. No. 7,816,344; b) an amino acid or a salt thereof.

In an exemplary embodiment, the invention provides a) a substituted benzoxaborole or salt thereof as described in U.S. Pat. No. 7,816,344; b) a naturally occurring amino acid or a salt thereof.

In an exemplary embodiment, the invention provides a) a substituted benzoxaborole or salt thereof as described in U.S. Pat. No. 7,816,344; b) a non-naturally occurring amino acid or a salt thereof.

In an exemplary embodiment, the invention provides a) a substituted benzoxaborole or salt thereof as described in U.S. Pat. No. 7,816,344; b) a naturally occurring amino acid or a salt thereof or a non-naturally occurring amino acid or a salt thereof, and/or a combination thereof.

In an exemplary embodiment, the invention provides a) a substituted benzoxaborole or a salt thereof as described in U.S. Pat. No. 7,816,344; b) at least one amino acid or a salt thereof having a structure according to the following formula:

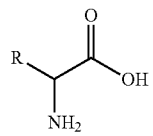

wherein R is a member selected from substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, or a salt thereof.

In an exemplary embodiment, the invention provides a) a substituted benzoxaborole or a salt thereof as described in U.S. Pat. No. 7,816,344; b) at least one amino acid having a structure selected from the group consisting of:

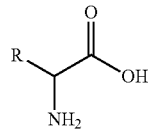

wherein R is methyl or ethyl or propyl or isopropyl or butyl or isobutyl or sec-butyl or t-butyl, wherein each is optionally substituted, with the exception of isobutyl which must be substituted with at least one methyl or ethyl or propyl or isopropyl or allyl or methylene or NH$_2$ or NH(CH$_3$) or NH(CH$_2$CH$_3$) or NH((CH$_2$)$_2$CH$_3$) or NH(CH(CH$_3$)$_2$) or NH((CH$_2$)$_3$CH$_3$) or NH(CH(CH$_3$)(CH$_2$)CH$_3$) or NH(C(CH$_3$)$_3$) or N(CH$_3$)$_2$ or N(CH$_3$)(CH$_2$CH$_3$) or N(CH$_2$CH$_3$)$_2$ or OH or OCH$_3$ or OCH$_2$CH$_3$ or O(CH$_2$)$_2$CH$_3$ or OCH(CH$_3$)$_2$ or O(CH$_2$)$_3$CH$_3$ or OCH(CH$_3$)(CH$_2$CH$_3$) or O(CH$_3$)$_3$ or SH or SCH$_3$ or SCH$_2$CH$_3$ or S(CH$_2$)$_2$CH$_3$ or SCH(CH$_3$)$_2$ or S(CH$_2$)$_3$CH$_3$ or SCH(CH$_3$)(CH$_2$CH$_3$) or S(CH$_3$)$_3$ or oxonorvaline

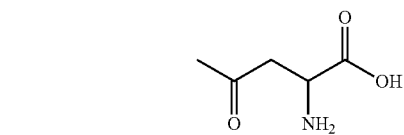

or a salt thereof.

In an exemplary embodiment, the invention provides a) a substituted benzoxaborole as described in U.S. Pat. No. 7,816,344; b) at least one amino acid having a structure selected from the group consisting of:

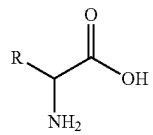

wherein R is cyclopropyl or cyclobutyl or cyclopentyl or (cyclopropyl)methyl or (cyclobutyl)methyl or (cyclopentyl)methyl or (cyclopropyl)ethyl or (cyclobutyl)ethyl or (cyclopentyl)ethyl, wherein each is optionally substituted with at least one methyl or ethyl or propyl or isopropyl or allyl or methylene or NH$_2$ or NH(CH$_3$) or NH(CH$_2$CH$_3$) or NH((CH$_2$)$_2$CH$_3$) or NH(CH(CH$_3$)$_2$) or NH((CH$_2$)$_3$CH$_3$) or NH(CH(CH$_3$)(CH$_2$)CH$_3$) or NH(C(CH$_3$)$_3$) or N(CH$_3$)$_2$ or N(CH$_3$)(CH$_2$CH$_3$) or N(CH$_2$CH$_3$)$_2$ or OH or OCH$_3$ or OCH$_2$CH$_3$ or O(CH$_2$)$_2$CH$_3$ or OCH(CH$_3$)$_2$ or O(CH$_2$)$_3$CH$_3$ or OCH(CH$_3$)(CH$_2$CH$_3$) or O(CH$_3$)$_3$ or SH or SCH$_3$ or SCH$_2$CH$_3$ or S(CH$_2$)$_2$CH$_3$ or SCH(CH$_3$)$_2$ or S(CH$_2$)$_3$CH$_3$ or SCH(CH$_3$)(CH$_2$CH$_3$) or S(CH$_3$)$_3$ oxonorvaline

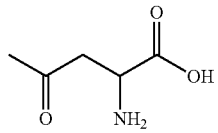

or a salt thereof.

In an exemplary embodiment, the amino acid is an amino acid described herein, and the amino acid is a D-amino acid. In an exemplary embodiment, the amino acid is an amino acid described herein, and the amino acid is a L-amino acid.

In an exemplary embodiment, the invention provides a) a substituted benzoxaborole or a salt thereof as described in U.S. Pat. No. 7,816,344; b) at least one amino acid or a salt thereof which is alanine or methallylglycine or norvaline or valine or norleucine or isoleucine or methionine or homocysteine or homoserine or cyclopropylglycine, or cyclopropylalanine or hypoglycine or azaleucine, and/or a combination thereof.

In an exemplary embodiment, the invention provides a) a substituted benzoxaborole or a salt thereof as described in U.S. Pat. No. 7,816,344; b) at least one amino acid or salt thereof which is norvaline, methionine, norleucine, isoleucine, homocysteine, homoserine or valine, and/or a combination thereof.

In an exemplary embodiment, the invention provides a) a substituted benzoxaborole or its salt as described in U.S. Pat. No. 7,816,344; b) norvaline, or a salt thereof.

In an exemplary embodiment, the invention provides a) a substituted benzoxaborole or salt thereof according to Formula II; b) at least one amino acid or a salt thereof. In an exemplary embodiment, the invention provides a) a substituted benzoxaborole according to Formula II; b) at least one naturally occurring amino acid or a salt thereof. In an exemplary embodiment, the invention provides a) a substituted benzoxaborole according to Formula II; b) at least one non-naturally occurring amino acid or a salt thereof. In an exemplary embodiment, the invention provides a) a substituted benzoxaborole according to Formula II; b) at least one naturally occurring amino acid or a non-naturally occurring amino acid, or combinations thereof or a salt thereof.

In an exemplary embodiment, the invention provides a) a substituted benzoxaborole according to Formula II; b) at least one amino acid which is norvaline, methionine, norleucine, isoleucine, homocysteine, homoserine or valine, and combinations thereof, or a salt thereof. In an exemplary embodiment, the invention provides a) a substituted benzoxaborole according to Formula II; b) norvaline, or a salt thereof.

In an exemplary embodiment, the invention provides a) a substituted benzoxaborole or a salt thereof having has a structure which is

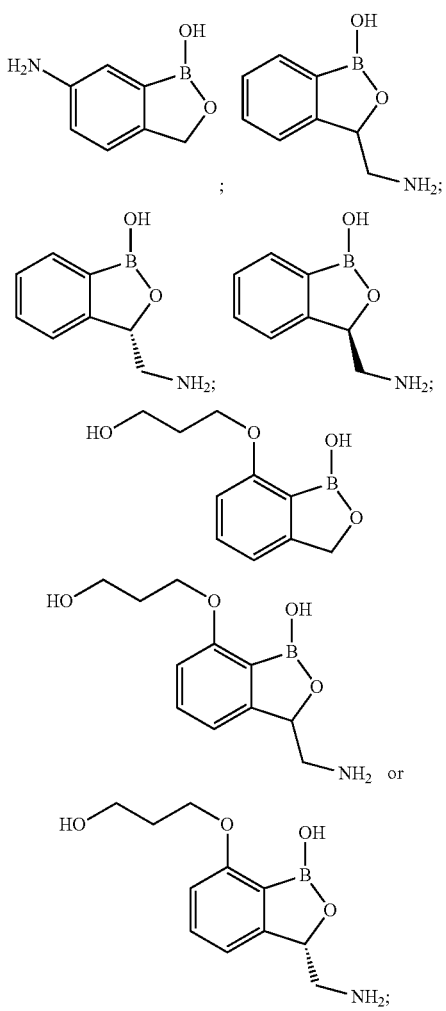

b) at least one amino acid or a salt thereof.

In an exemplary embodiment, the invention provides a) a substituted benzoxaborole or a salt thereof having has a structure which is

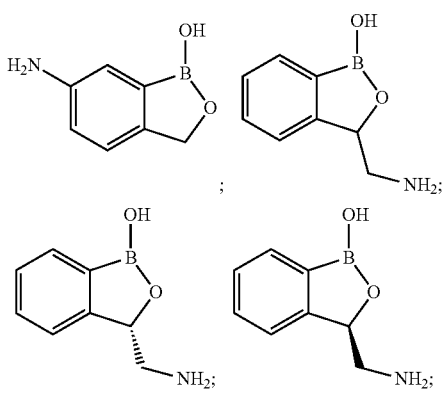

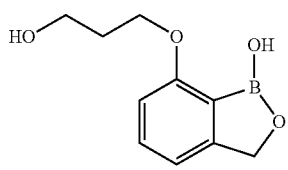

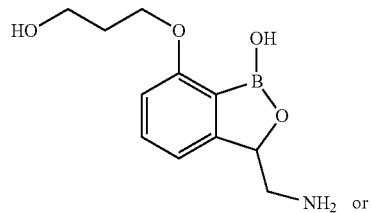

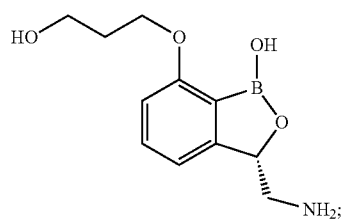

b) at least one naturally occurring amino acid or a salt thereof.

In an exemplary embodiment, the invention provides a) a substituted benzoxaborole or a salt thereof having has a structure which is

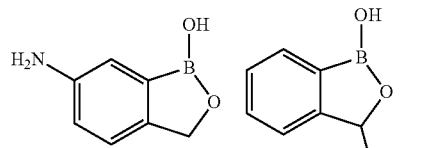

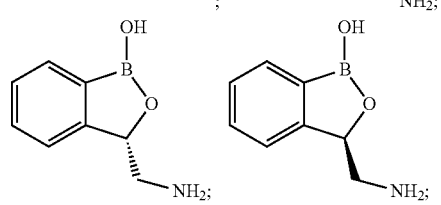

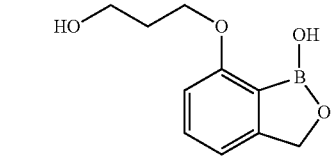

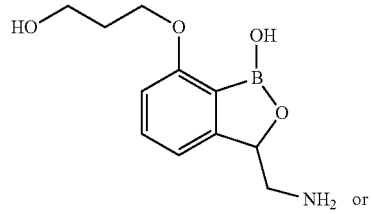

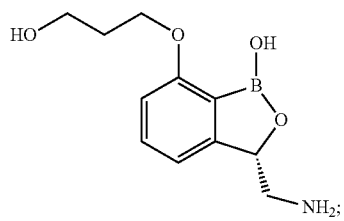

b) at least one non-naturally occurring amino acid or a salt thereof.

In an exemplary embodiment, the invention provides a) a substituted benzoxaborole or a salt thereof having has a structure which is

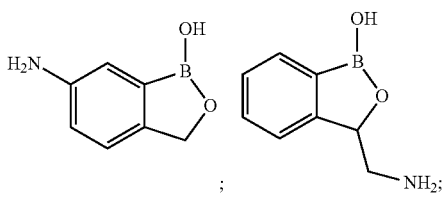

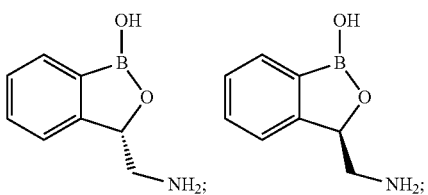

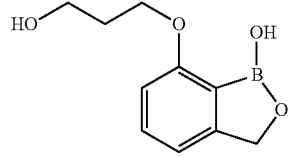

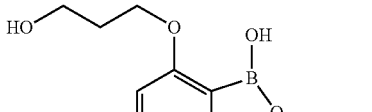

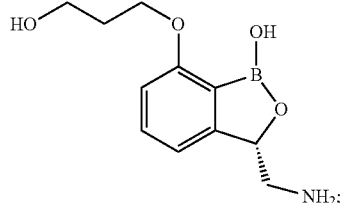

b) at least one naturally occurring amino acid or a non-naturally occurring amino acid, or combinations thereof or a salt thereof.

In an exemplary embodiment, the invention provides a) a substituted benzoxaborole or a salt thereof having has a structure which is

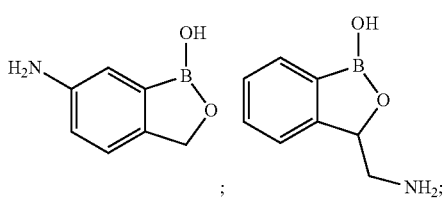

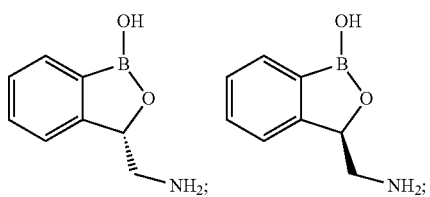

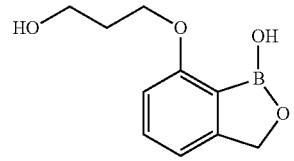

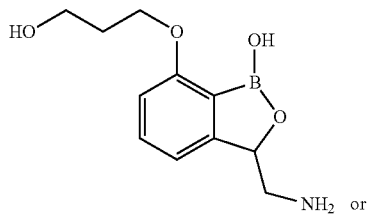

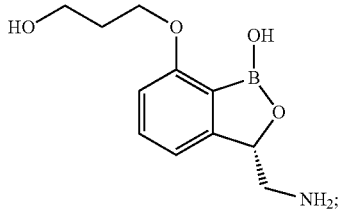

b) at least one amino acid or a salt thereof which is norvaline, methionine, norleucine, isoleucine, homocysteine, homoserine or valine, and combinations thereof.

In an exemplary embodiment, the invention provides a) a substituted benzoxaborole or a salt thereof having has a structure which is

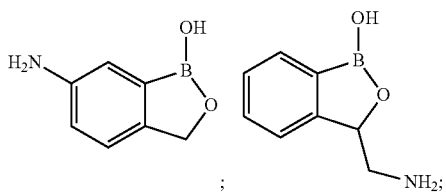

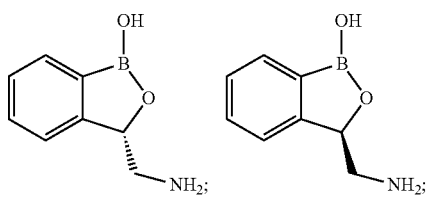

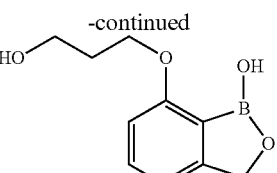

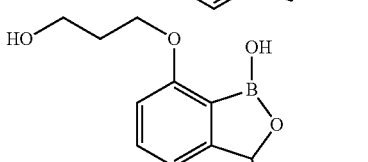

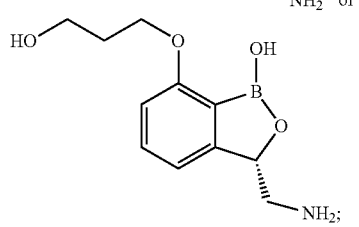

b) norvaline, or a salt thereof.

In an exemplary embodiment, the invention provides a) GSK2251052 or a salt thereof; b) at least one amino acid or a salt thereof. In an exemplary embodiment, the invention provides a) GSK2251052 or a salt thereof; b) at least one naturally occurring amino acid or a salt thereof. In an exemplary embodiment, the invention provides a) GSK2251052 or a salt thereof; b) at least one non-naturally occurring amino acid or a salt thereof. In an exemplary embodiment, the invention provides a) GSK2251052 or a salt thereof; b) at least one naturally occurring amino acid or a non-naturally occurring amino acid, or combinations thereof or a salt thereof. In an exemplary embodiment, the invention provides a) GSK2251052 or a salt thereof; b) at least one amino acid which is norvaline, methionine, norleucine, isoleucine, homocysteine, homoserine or valine, and combinations thereof, or a salt thereof. In an exemplary embodiment, the invention provides a) GSK2251052 or a salt thereof; b) norvaline or a salt thereof.

In an exemplary embodiment, the substituted benzoxaborole in the combination is described herein, or is a salt, prodrug, hydrate or solvate thereof, or a combination thereof. In an exemplary embodiment, the substituted benzoxaborole in the combination is described herein, or is a salt, hydrate or solvate thereof. In an exemplary embodiment, the substituted benzoxaborole in the combination is described herein, or a prodrug thereof. In an exemplary embodiment, the substituted benzoxaborole in the combination is described herein, or is a salt thereof. In another exemplary embodiment, the substituted benzoxaborole in the combination is described herein, or is a pharmaceutically acceptable salt thereof. In an exemplary embodiment, the combination is part of a pharmaceutical formulation described herein. Such conditions are known to one skilled in the art and specific conditions are set forth in the Examples appended hereto.

In an exemplary embodiment, the amino acid in the combination is described herein, or is a salt, hydrate or solvate thereof, or a combination thereof. In an exemplary embodiment, the amino acid in the combination is described herein, or is a salt thereof. In another exemplary embodiment, the amino acid in the combination is described herein, or a is pharmaceutically acceptable salt thereof. In an exemplary embodiment, for any amino acid described herein, the amino acid is a D-amino acid. In an exemplary embodiment, for any amino acid described herein, the amino acid is a L-amino acid.

In an exemplary embodiment, for any of the combinations described herein, there is a) substituted benzoxaborole or a salt thereof described herein; b) an amino acid or a salt thereof described herein. In an exemplary embodiment, for any of the combinations described herein, there is a) substituted benzoxaborole or a salt thereof described herein; b) a first amino acid or a salt thereof, selected from an amino acid described herein; and c) a second amino acid or a salt thereof, selected from an amino acid described herein. In an exemplary embodiment, for any of the combinations described herein, there is a) substituted benzoxaborole or a salt thereof described herein; b) a first amino acid or a salt thereof, selected from an amino acid described herein; c) a second amino acid or a salt thereof, selected from an amino acid described herein; d) a third amino acid or a salt thereof, selected from an amino acid described herein. In an exemplary embodiment, for any of the combinations described herein, there is a) substituted benzoxaborole or a salt thereof described herein; b) a first amino acid or a salt thereof, selected from an amino acid described herein; c) a second amino acid or a salt thereof, selected from an amino acid described herein; d) a third amino acid or a salt thereof, selected from an amino acid described herein; d) a fourth amino acid or a salt thereof, selected from an amino acid described herein.

In an exemplary embodiment, the combination is part of a pharmaceutical formulation described herein. Such conditions are known to one skilled in the art and specific conditions are set forth in the Examples appended hereto.

IIa. Dosage Forms of the Combination

The individual components of the combinations of the invention, for example, a combination described herein, may be administered either simultaneously or sequentially in a unit dosage form. The unit dosage form may be a single or multiple unit dosage form. In an exemplary embodiment, the invention provides a combination in a single unit dosage form. An example of a single unit dosage form is a capsule wherein both the substituted benzoxaborole and the amino acid are contained within the same capsule. In an exemplary embodiment, the invention provides a combination in a two unit dosage form. An example of a two unit dosage form is a first capsule which contains the substituted benzoxaborole and a second capsule which contains the amino acid. Thus the term 'single unit' or 'two unit' or 'multiple unit' refers to the object which the subject ingests, not to the interior components of the object. Appropriate doses of substituted benzoxaboroles will be readily appreciated by those skilled in the art. Appropriate doses of amino acids will be readily appreciated by those skilled in the art. In an exemplary embodiment, the substituted benzoxaborole is present in the combination in a therapeutically effective amount. In an exemplary embodiment, the amino acid is present in the combination in an amount sufficient to reduce the rate of and/or decrease the frequency of and/or suppress the emergence of resistance in bacteria exposed to the substituted benzoxaborole, IIb. Additional Therapeutic Agent(s) in the Combination The combinations of the invention, for example, a combination described herein, may also include an additional therapeutic agent or therapeutic agents. The invention thus provides, in a further aspect, a combination comprising a substituted benzoxaborole described herein or a pharmaceutically acceptable salt thereof, an amino acid described herein or a pharmaceutically acceptable salt thereof, and at least one additional therapeutic agent. The invention thus provides, in a further aspect, a combination comprising a substituted benzoxaborole described herein or a pharmaceutically acceptable salt thereof, norvaline or a pharmaceutically acceptable salt thereof, and at least one additional therapeutic agent. In an exemplary embodiment, the additional therapeutic agent is as described in U.S. Pat. No. 7,816,344. In an exemplary embodiment, the additional therapeutic agent is an antibacterial agent. In one aspect, the invention comprises: a) a combination of the invention; and b) at least one additional therapeutic agent. In another exemplary embodiment, the invention comprises: a) a combination of the invention; b) a first additional therapeutic agent; and c) a second additional therapeutic agent. In another exemplary embodiment, the invention comprises: a) a combination of the invention; b) a first additional therapeutic agent; c) a second additional therapeutic agent; and d) a third additional therapeutic agent. The first additional therapeutic agent or second additional therapeutic agent or third additional therapeutic agent may be selected from the additional therapeutic agents described herein.

When an additional therapeutic agent is used with a combination of the invention against the same disease state, the dose of each compound may differ from that when the compound is used alone. Appropriate doses will be readily appreciated by those skilled in the art. It will be appreciated that the amount of a compound of the invention required for use in treatment will vary with the nature of the condition being treated and the age and the condition of the subject and will be ultimately at the discretion of the attendant physician or veterinarian.

IIc. Preparation of Boron-Containing Compounds

Compounds of use in the invention can be prepared using commercially available starting materials, known intermediates, or by using the synthetic methods described herein, or published in references described and incorporated by reference herein, such as U.S. Pat. No. 7,816,344 and PCT Pat. Pubs. WO2010080558 and WO2011127143

III. Methods of Inhibiting Bacterial Growth or Killing Bacteria

The combinations of the invention exhibit potency against bacteria and therefore have the potential to kill and/or inhibit the growth of bacteria. The combinations of the invention exhibit potency against bacteria possessing a LeuRS with or without a mutated or absent editing-domain and thus have the potential to kill and/or inhibit such "resistant bacteria".

In a further aspect, the invention provides a method of killing and/or inhibiting the growth of a bacteria, said method comprising: contacting said bacteria with an effective amount of a combination of the invention, thereby killing and/or inhibiting the growth of the bacteria. In an exemplary embodiment, the combination is part of a pharmaceutical formulation described herein. In another exemplary embodiment, the contacting occurs under conditions which permit entry of the combination into the organism.

In another aspect, the bacteria is on the surface of an animal. In another aspect, the bacteria is in an animal.

In an exemplary embodiment, the bacteria is killed or its growth is inhibited through oral administration of the combination of the invention. In an exemplary embodiment, the bacteria is killed or its growth is inhibited through intravenous administration of the combination of the invention. In an exemplary embodiment, the bacteria is killed or its growth is inhibited through subcutaneous administration of the combination of the invention.

In exemplary embodiments, the bacteria contacted with a combination of the invention comprising a substituted benzoxaborole or salt thereof and an amino acid or salt thereof is a population of bacteria comprising a resistant bacterium with a mutation conferring resistance to the substituted benzoxaborole, In a particular embodiment, the population of bacteria comprises a resistant bacterium with a mutation in the editing domain of a bacteria LeuRS.

In an exemplary embodiment, the bacteria is described in U.S. Pat. No. 7,816,344.

In another exemplary embodiment, the bacterium is a gram-positive bacterium. In another exemplary embodiment, the bacterium is a gram-negative bacterium. In another exemplary embodiment, the gram-negative bacterium is a member selected from *Acinetobacter* species, *Neisseria* species, *Pseudomonas* species, *Brucella* species, *Agrobacterium* species, *Bordetella* species, *Escherichia* species, *Shigella* species, *Yersinia* species, *Salmonella* species, *Klebsiella* species, *Enterobacter* species, *Haemophilus* species, *Pasteurella* species, *Streptobacillus* species, spirochetal species, *Campylobacter* species, *Vibrio* species, *Helicobacter* species, *Bacteroides* species, *Citrobacter* species, *Proteus* species, *Providencia* species, *Serratia* species, *Stenotrophomonas* species and *Burkholderia* species. In another exemplary embodiment, the gram-negative bacterium is a member selected from *Acinetobacter* species, *Pseudomonas* species, *Escherichia* species, *Klebsiella* species, *Enterobacter* species, *Bacteroides* species, *Citrobacter* species, *Proteus* species, *Providencia* species, *Serratia* species, *Stenotrophomonas* species and *Burkholderia* species. In another exemplary embodiment, the gram-negative bacterium is a member selected from *Neisseria gonorrhoeae; Neisseria meningitidis; Pseudomonas aeruginosa; Legionella pneumophila; Escherichia coli; Yersinia pestis; Haemophilus influenzae; Helicobacter pylori; Campylobacter fetus; Campylobacter jejuni; Vibrio cholerae; Vibrio parahemolyticus; Treponema pallidum; Actinomyces israelii; Rickettsia prowazekii; Rickettsia rickettsii; Chlamydia trachomatis; Chlamydia psittaci; Brucella abortus; Agrobacterium tumefaciens; Francisella tularensis, Klebsiella pneumoniae, Enterobacter cloacae, Acinetobacter baumannii, Bacteroides fragilis, Citrobacter freundii, Proteus mirabilis, Providencia stuartii, Serratia marcescens, Stenotrophomonas maltophilia* and *Burkholderia cepacia*. In another exemplary embodiment, the gram-negative bacterium is a member selected from *Pseudomonas aeruginosa; Escherichia coli; Haemophilus influenzae, Klebsiella pneumoniae, Enterobacter cloacae, Acinetobacter baumannii, Bacteroides fragilis, Citrobacter freundii, Proteus mirabilis, Providencia stuartii, Serratia marcescens, Stenotrophomonas maltophilia* and *Burkholderia cepacia*.

In another exemplary embodiment, the bacterium is a *Pseudomonas* species. In another exemplary embodiment, the bacterium is *Pseudomonas aeruginosa*. In another exemplary embodiment, the bacterium is a member selected from *Pseudomonas aeruginosa; Acinetobacter baumannii, Stenotrophomonas maltophilia* and *Burkholderia cepacia*. In another exemplary embodiment, the bacterium is *Acinetobacter* species. In another exemplary embodiment, the bacterium is *Acinetobacter anitratus*. In another exemplary embodiment, the bacterium is a member selected from *Enterobacter aerogenes, Enterobacter cloacae, Enterobacter sakazakii, E. coli, K. pneumoniae, P. mirabilis, Serratia marcescens, Citrobacter freundii* and *Providencia* spp. In another exemplary embodiment, the bacterium is a member selected from *Enterobacter aerogenes, Enterobacter cloacae, Enterobacter sakazakii, E. coli, K. pneumoniae, P. mirabilis, Serratia marcescens, Citrobacter freundii, Providencia* spp., *S. aureus, S. pneumonia, S. pyogenes, E. faecalis*, and *E. faecium*. In another exemplary embodiment, the bacterium is a member selected from *Viridans* group Strep. In another exemplary embodiment, the bacterium is a member selected from *Strep. mitis, Strep. mutans, Strep. oralis, Strep. sanguis, Strep. sobrinus* and *Strep. millari*. In another exemplary embodiment, the bacterium is a member selected from *S. pneumonia, H. influenzae, S. aureus, M. catarrhalis, M. pneumoniae, L. pneumoniae* and *C. pneumoniae*. In another exemplary embodiment, the bacterium is *S. aureus*. In another exemplary embodiment, the bacterium is an anaerobe. In another exemplary embodiment, the bacterium is an *Alcaligenes* species. In another exemplary embodiment, the bacterium is a *B. cepacia*. In another exemplary embodiment, the bacterium is a member selected from *Enterobacter cloacae, Escherichia coli; Klebsiella pneumoniae, Proteus mirabilis, Providencia stuartii, Serratia marcescens*, and *Citrobacter freundii*. In another exemplary embodiment, the bacterium is resistant to methicillin. In another exemplary embodiment, the bacterium is methicillin-resistant *staphylococcus aureus*. In another exemplary embodiment, the bacterium is a member selected from *Streptococcus pneumoniae; Haemophilus influenzae; Staphylococcus aureus; Moraxella catarrhalis; Mycoplasma pneumoniae; Legionella pneumophila* and *Chlamydia pneumoniae*. In another exemplary embodiment, the bacterium is a member selected from *Enterobacter cloacae, Escherichia coli; Klebsiella pneumoniae, Proteus mirabilis, Serratia marcescens, Citrobacter freundii, Providencia stuartii, Pseudomonas aeruginosa; Acinetobacter baumannii, Stenotrophomonas maltophilia, Burkholderia cepacia, Staphylococcus aureus; Streptococcus pneumoniae; Streptococcus pyogenes; Enterococcus faecalis*; and *Enterococcus faecium*.

In an exemplary embodiment, the bacteria in the methods described herein comprises a resistant bacterium. In an exemplary embodiment, the resistant bacterium is a mutation of a bacteria described herein. In an exemplary embodiment, the resistant bacterium possesses a mutation conferring resistance to a substituted benzoxaborole or salt thereof, as described herein. In an exemplary embodiment, the mutation conferring resistance possesses a mutated LeuRS. In an exemplary embodiment, the resistant bacterium possesses a LeuRS with a mutated editing domain. In an exemplary embodiment, the resistant bacterium is a species of gram-negative bacteria.

IV. Methods of Treating and/or Preventing Disease

The combinations of the present invention exhibit potency against bacteria, and therefore have the potential to achieve therapeutic efficacy in the animals described herein.

In another aspect, the invention provides a method of treating and/or preventing a disease. The method includes administering to the animal a therapeutically effective amount of a combination of the invention, sufficient to treat and/or prevent the disease. In an exemplary embodiment, the combination of the invention can be used in human or veterinary medical therapy, particularly in the treatment or prophylaxis of bacterial-associated disease. In an exemplary embodiment, the combination is described herein.

In another exemplary embodiment, the animal is as defined herein. In another exemplary embodiment, the disease a systemic disease or a cutaneous disease. In another exemplary embodiment, the disease is a systemic disease. In another exemplary embodiment, In an exemplary embodiment, the substituted benzoxaborole in the combination has a structure which is

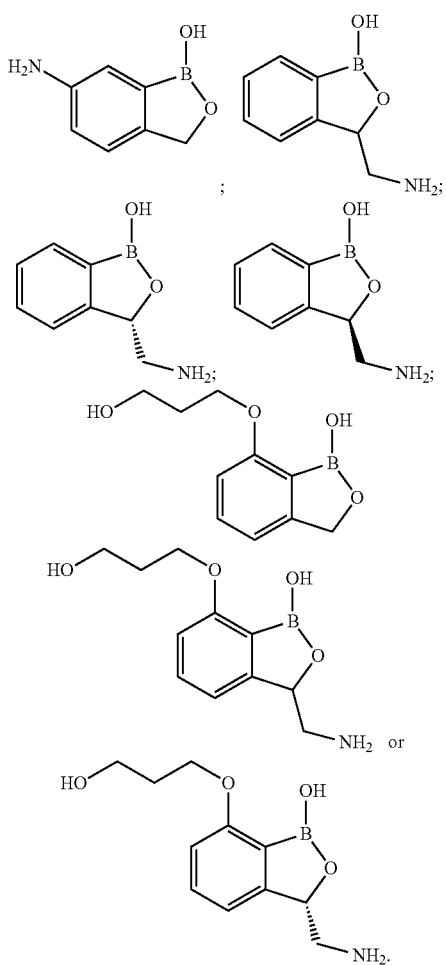

In an exemplary embodiment, the compound is

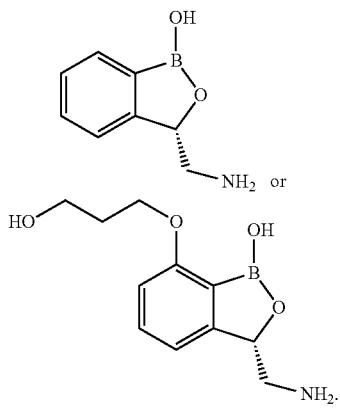

In another exemplary embodiment, the treatment of a disorder or condition occurs through inhibition of an editing domain of an aminoacyl tRNA synthetase. In another exemplary embodiment, the treatment of a disorder or condition occurs through insertion of amino acids from mischarged tRNA$^{Leu}$ into proteins of the bacteria. In another exemplary embodiment, the treatment of a disorder or condition occurs through inhibition of an editing domain of an aminoacyl tRNA synthetase and through insertion of amino acids from mischarged tRNA$^{Leu}$ into proteins of the bacteria.

In an exemplary embodiment, the disease is treated through oral administration of the combination of the invention. In an exemplary embodiment, the disease is treated through intravenous administration of the combination of the invention.

IVa. Methods of Treating Systemic Diseases

In another aspect, the invention provides a method of treating a systemic disease. The method involves contacting an animal with a combination of the invention.

In an exemplary embodiment, the disease is associated with an infection by a bacterium described herein. In an exemplary embodiment, the disease is associated with an infection by a resistant bacterium described herein. In an exemplary embodiment, the disease is associated with an infection by a resistant bacterium which possesses a mutated LeuRS. In an exemplary embodiment, the disease is associated with an infection by a resistant bacterium which possesses a LeuRS with a mutated editing domain. In an exemplary embodiment, the disease is associated with an infection by a resistant Gram-negative bacteria.

In another exemplary embodiment, the disease is associated with infection by a Gram-negative bacteria. In an exemplary embodiment, the disease is associated with a *Neisseria* species. In another exemplary embodiment, the disease is a member selected from meningitis, gonorrhea, otitis extema and folliculitis. In an exemplary embodiment, the disease is associated with an *Escherichia* species. In another exemplary embodiment, the disease is a member selected from diarrhea, urinary tract infections, meningitis, sepsis and HAP. In an exemplary embodiment, the disease is associated with a *Shigella* species. In another exemplary embodiment, the disease is a member selected from diarrhea, bacteremia, endocarditis, meningitis and gastroenteritis. In an exemplary embodiment, the disease is associated with a *Salmonella* species. In another exemplary embodiment, the disease is a member selected from Typhoid fever, sepsis, gastroenteritis, endocarditis, sinusitis and meningitis. In an exemplary embodiment, the disease is associated with a *Yersinia* species. In another exemplary embodiment, the disease is a member selected from Typhoid fever, bubonic plague, enteric fever and gastroenteritis. In an exemplary embodiment, the disease is associated with a *Klebsiella* species. In another exemplary embodiment, the disease is a member selected from sepsis and urinary tract infection. In an exemplary embodiment, the disease is associated with a *Proteus* species. In another exemplary embodiment, the disease is an urinary tract infection. In an exemplary embodiment, the disease is associated with an *Enterobacter* species. In another exemplary embodiment, the disease is a hospital-acquired infection. In an exemplary embodiment, the disease is associated with a *Serratia* species. In another exemplary embodiment, the disease is a member selected from a urinary tract infection, skin and skin-structure infection and pneumonia. In an exemplary embodiment, the disease is associated with a *Vibrio* species. In another exemplary embodiment, the disease is a member selected from cholera and gastroenteritis. In an exemplary embodiment, the disease is associated with a *Campylobacter* species. In another exemplary embodiment, the disease is gastroenteritis. In an exemplary embodiment, the disease is associated with a *Helicobacter* species. In another exemplary embodiment, the disease is chronic gastritis. In an exemplary embodiment, the disease is associated with a *Pseudomonas* species. In another exemplary embodiment, the disease is a member selected from pneumonia, osteomylitis, burn-wound infections, sepsis, UTIs, endocarditis, otitis, corneal infections. In an exemplary embodiment, the disease is associated with a *Bacteroides* species. In another exemplary embodiment, the disease is a member selected from periodontal disease and aspriation pneumonia. In an exemplary embodiment, the disease is associated with a *Haemophilus* species. In another exemplary embodiment, the disease is a member selected from meningitis, epiglottitis, septic arthritis, sepsis, chancroid and vaginitis. In an exemplary embodiment, the disease is associated with a *Bordetella* species. In another exemplary embodiment, the disease is Whooping cough. In an exemplary embodiment, the disease is associated with a *Legionella* species. In another exemplary embodiment, the disease is a member selected from pneumonia and pontiac fever. In an exemplary embodiment, the disease is associated with a *Francisella* species. In another exemplary embodiment, the disease is tularemia. In an exemplary embodiment, the disease is associated with a *Brucella* species. In another exemplary embodiment, the disease is brucellosis. In an exemplary embodiment, the disease is associated with a *Pasteurella* species. In another exemplary embodiment, the disease is a skin infection. In an exemplary embodiment, the disease is associated with a *Gardnerella* species. In another exemplary embodiment, the disease is vaginitis. In an exemplary embodiment, the disease is associated with a Spirochetes species. In another exemplary embodiment, the disease is syphilis and Lyme disease. In an exemplary embodiment, the disease is associated with a *Chlamydia* species. In another exemplary embodiment, the disease is *chlamydia*. In an exemplary embodiment, the disease is associated with a *Rickettsiae* species. In another exemplary embodiment, the disease is a member selected from Rocky Mountain spotted fever and typhus.

In an exemplary embodiment, the disease is associated with *Mycoplasma pneumoniae*. In another exemplary embodiment, the disease is a member selected from tracheobronchitis and walking pneumonia. In an exemplary embodiment, the disease is associated with *Ureaplasma urealyticum*. In another exemplary embodiment, the disease is urethritis. In another exemplary embodiment, the disease is pyelonenephritis. In another exemplary embodiment, the disease is an intra-abdominal infection. In another exemplary embodiment, the disease is febrile neutropenia. In another exemplary embodiment, the disease is a pelvic infection. In another exemplary embodiment, the disease is bacteraemia. In another exemplary embodiment, the disease is septicaemia.

In an exemplary embodiment, the disease is treated through oral administration of the combination of the invention. In an exemplary embodiment, the disease is treated through intravenous administration of the combination of the invention. In an exemplary embodiment, the disease is treated through topical administration of the combination of the invention. In an exemplary embodiment, the disease is treated through intraperitoneal administration of the combination of the invention. In an exemplary embodiment, the disease is treated through subcutaneous injection of the combination of the invention. In an exemplary embodiment, the combination is administered in a topically effective amount. In an exemplary embodiment, the pharmaceutical formulation is administered in an orally effective amount. In an exemplary embodiment, the combination is administered in an effective amount via subcutaneous injection.

In another aspect, the invention provides a method of decreasing the frequency of and/or reducing the rate of and/or suppressing the emergence of resistance in a population of bacteria to a substituted benzoxaborole described herein. In an exemplary embodiment, the method comprises administering a combination described herein to an animal with a bacterial infection, thereby decreasing the frequency of resistance.

V. Animals

In another exemplary embodiment, the animal of any of the methods described herein is a member selected from human, cattle, deer, reindeer, goat, honey bee, pig, sheep, horse, cow, bull, dog, guinea pig, gerbil, rabbit, cat, camel, yak, elephant, ostrich, otter, chicken, duck, goose, guinea fowl, pigeon, swan, and turkey. In another exemplary embodiment, the animal is a human. In another exemplary embodiment, the animal is a non-human mammal. In another exemplary embodiment, the animal is a mammal. In another exemplary embodiment, the animal is a domestic animal. In another exemplary embodiment, the animal is a domestic mammal. In another exemplary embodiment, the animal is a companion animal. In another exemplary embodiment, the animal is a companion mammal. In another exemplary embodiment, the animal is a dog. In another exemplary embodiment, the animal is a cat. In another exemplary embodiment, the animal is a rodent. In another exemplary embodiment, the animal is a rat. In another exemplary embodiment, the animal is a mouse. In another exemplary embodiment, the animal is a member selected from goat, pig, sheep, horse, cow, bull, dog, guinea pig, gerbil, rabbit, cat, chicken and turkey. In another exemplary embodiment, the animal is an ungulate. In another exemplary embodiment, the ungulate is selected from the group consisting of horse, zebra, donkey, cattle/bison, rhinoceros, camel, hippopotamus, goat, pig, sheep, giraffe, okapi, moose, elk, deer, tapir, antelope, and gazelle. In another exemplary embodiment, the ungulate is cattle. In another exemplary embodiment, the ungulate is selected from the group consisting of goat, pig, and sheep. In another exemplary embodiment, the animal is a ruminant. In another exemplary embodiment, the ruminant is selected from the group consisting of cattle, goats, sheep, giraffes, bison, yaks, water buffalo, deer, camels, alpacas, llamas, wildebeest, antelope, pronghorn, and nilgai. In another exemplary embodiment, the cattle is a cow. In another exemplary embodiment, the cattle is a bull. In another exemplary embodiment, the cattle is a calf. In another exemplary embodiment, the animal is an equine. In another exemplary embodiment, the animal is selected from the group consisting of horse, donkey, caribou and reindeer. In another exemplary embodiment, the animal is a horse.

VI. Pharmaceutical Formulations

In another aspect, the invention is a pharmaceutical formulation which includes: (a) a pharmaceutically acceptable excipient; (b) a combination of the invention. In another aspect, the pharmaceutical formulation includes: (a) a pharmaceutically acceptable excipient; and (b) a combination described herein. In another aspect, the pharmaceutical formulation includes: (a) a pharmaceutically acceptable excipient; and (b) a combination described herein, or a salt, prodrug, hydrate or solvate thereof. In another aspect, the pharmaceutical formulation includes: (a) a pharmaceutically acceptable excipient; and (b) a combination described herein, or a salt, hydrate or solvate thereof. In another aspect, the pharmaceutical formulation includes: (a) a pharmaceutically acceptable excipient; and (b) a combination described herein, or a salt, hydrate or solvate thereof. In another aspect, the pharmaceutical formulation includes: (a) a pharmaceutically acceptable excipient; and (b) a salt of a combination described herein. In an exemplary embodiment, the salt is a pharmaceutically acceptable salt. In another aspect, the pharmaceutical formulation includes: (a) a pharmaceutically acceptable excipient; and (b) a prodrug of a combination described herein. In another aspect, the pharmaceutical formulation includes: (a) a pharmaceutically acceptable excipient; and (b) a combination described herein. In an exemplary embodiment, the pharmaceutical formulation is a unit dosage form. In an exemplary embodiment, the pharmaceutical formulation is a single unit dosage form.

In an exemplary embodiment, the pharmaceutical formulation is a unit dosage form. In an exemplary embodiment, the pharmaceutical formulation is a single unit dosage form. In an exemplary embodiment, the pharmaceutical formulation is a two unit dosage form. In an exemplary embodiment, the pharmaceutical formulation is a two unit dosage form comprising a first unit dosage form and a second unit dosage form, wherein the first unit dosage form includes a) a compound of the invention and b) a first pharmaceutically acceptable excipient; and the second unit dosage form includes c) an additional therapeutic agent and d) a second pharmaceutically acceptable excipient.

Information regarding excipients of use in the formulations of the invention can be found in Remington: The Science and Practice of Pharmacy, 21st Ed., Pharmaceutical Press (2011) which is incorporated herein by reference.

The invention is further illustrated by the Examples that follow. The Examples are not intended to define or limit the scope of the invention.

EXAMPLES

Example 1

Resistant Mutants to GSK2251052 Generated In Vitro

Spontaneous Resistance Frequency was determined in vitro for GSK2251052 and the resistance mutants in E. coli ATCC 25922, K. pneumoniae ATCC 13883, and P. aeruginosa ATCC 27853 strains were characterized. GSK2251052 was prepared as described in U.S. Pat. No. 7,816,344 (the entire contents of which are hereby incorporated by reference herein). LB broth, Mueller Hinton II broth (adjusted), and Difco noble agar were obtained from Becton Dickinson (Cockeysville, Md., USA). M9 minimal broth containing 1×M9 salt, 0.5 µg/ML thiamine, 1 mM $MgSO_4$, 0.1 mM $CaCl_2$, 2% glucose, was obtained from Teknova (Hollister, Calif., USA). Antibacterial agents ciprofloxacin, ceftazidime, chloramphenicol, gentamycin, kanamycin, polymixin B, tobramycin and trimethoprim, and amino acids were obtained from Sigma Chemicals (St. Louis, Mo., USA). Strains were obtained from ATCC (Manassas, Va., USA).

Determination of the Minimum Inhibitory Concentration.

Susceptibility tests were performed following the recommendations for aerobic bacteria (M7-A7) from the Clinical and Laboratories Standards Institute (CLSI).

The MICs against E. coli ATCC 25922, K. pneumoniae ATCC 13883 and P. aeruginosa ATCC 27853 ranged from 1 to 4 µg/mL (Table 1).

Determination of the Spontaneous Frequency of Resistance.

Selection of resistance to GSK2251052 was attempted by spreading various amounts of bacteria onto MHBII noble agar plates containing 4×MIC (minimum inhibitory concentration) or 10×MIC of GSK2251052. Colonies were counted after 24 hours and 48 hours incubation at 37° C. The resistance of these colonies was confirmed by their ability to grow on plates containing GSK2251052 at either 4× or 10×MIC. Frequency of resistance was determined by dividing the number of resistant mutants by the total number of cells plated as determined by plating dilutions of the overnight culture on LB plates.

GSK2251052 shows a frequency of resistance of between $10^{-7}$ to $10^{-8}$ when measured at 24 h (Table 3). As seen in Table 3, the frequencies or resistance seen for GSK2251052 are comparable to that seen with other antibacterial agents.

TABLE 3

GSK2251052: Pre-Clinical In vitro Frequency of Resistance vs Standard Comparator Antibiotics

| | Frequency of Resistance | | | | | |
|---|---|---|---|---|---|---|
| | E. coli | | K. pneumoniae | | P. aeruginosa | |
| Compound | 4 X MIC | 10 X MIC | 4 X MIC | 10 X MIC | 4 X MIC | 10 X MIC |
| GSK2251052 | $8 \times 10^{-8}$ | $6 \times 10^{-8}$ | $5 \times 10^{-8}$ | $4 \times 10^{-8}$ | $1 \times 10^{-7}$ | $5 \times 10^{-8}$ |
| | $2 \times 10^{-7}$ | $7 \times 10^{-8}$ | $8 \times 10^{-7}$ | $6 \times 10^{-8}$ | $2 \times 10^{-7}$ | $9.6 \times 10^{-8}$ |
| | $1 \times 10^{-7}$ | $8 \times 10^{-8}$ | $4 \times 10^{-8}$ | $2 \times 10^{-8}$ | | |
| Ceftazidime | $<3 \times 10^{-9}$ | $<3 \times 10^{-9}$ | $1 \times 10^{-8}$ | $<4 \times 10^{-9}$ | $2 \times 10^{-7}$ | $2 \times 10^{-8}$ |
| Ciprofloxacin | $2 \times 10^{-8}$ | $<4 \times 10^{-9}$ | $5 \times 10^{-7}$ | $<5 \times 10^{-9}$ | $1 \times 10^{-8}$ | $<1 \times 10^{-9}$ |
| Levofloxacin | $2 \times 10^{-8}$ | $<5 \times 10^{-9}$ | $2 \times 10^{-7}$ | $<3 \times 10^{-9}$ | $1 \times 10^{-7}$ | $<1 \times 10^{-9}$ |
| Meropenem | $<4 \times 10^{-9}$ | $<4 \times 10^{-9}$ | $<3 \times 10^{-9}$ | $<3 \times 10^{-9}$ | $7 \times 10^{-7}$ | $<1 \times 10^{-9}$ |
| Tobramycin | $1 \times 10^{-5}$ | $4 \times 10^{-6}$ | $1 \times 10^{-6}$ | $5 \times 10^{-8}$ | $1 \times 10^{-6}$ | $9 \times 10^{-8}$ |

Laboratory generated mutants resistant to GSK2251052 contain mutations in the editing domain of LeuRS. Six to ten GSK2251052 resistant colonies of E. coli ATCC 25922, K. pneumoniae ATCC 13883 and P. aeruginosa ATCC 27853 were selected for further analysis and their MICs to GSK2251052 were determined (Table 4-7).

TABLE 4

MIC values determined for E. coli ATCC 25922 wild type and resistant mutants to GSK2251052 and mutations found in the editing domain of leuRS

| E. coli ATCC 25922 wild type and mutants | MIC (ug/mL) GSK2251052 | Location of mutation in leuRS |
|---|---|---|
| E wt | 1 | none |
| E101 | 64 | Y246H |
| E102 | 256 | D345G |
| E103 | 256 | " |
| E104 | 64 | Y246H |
| E105 | 256 | D345G |
| E106 | 256 | D345G |
| E107 | >256 | G229S |
| E108 | 256 | D345G |
| E109 | 256 | " |
| E110 | >256 | Duplication D345 Y346 |

TABLE 5

MIC values determined for P. aeruginosa ATCC27853 wild type and resistant mutants to GSK2251052 and mutations found in the editing domain of leuRS

| P. aeruginosa ATCC 27853 wild type and mutants | MIC (ug/mL) GSK2251052 | Location of mutation in leuRS |
|---|---|---|
| P wt | 4 | none |
| P101 | 128 | T256P |
| P102 | 32 | " |
| P103 | 64 | " |
| P104 | 128 | " |
| P105 | 128 | " |
| P106 | >256 | V342M |
| P107 | 128 | " |
| P108 | 128 | T252P |
| P109 | 128 | V342M |
| P110 | >256 | " |

TABLE 6

MIC values determined for K. pneumoniae ATCC13883 wild type and resistant mutants to GSK2251052 and mutations found in the editing domain of leuRS

| K. pneumoniae ATCC 13883 wild type and mutants | MIC (ug/mL) GSK2251052 | Location of mutation in leuRS |
|---|---|---|
| K wt | 1 | none |
| K104 | >256 | D345Y |
| K105 | >256 | G229R |
| K107 | 256 | S227F |
| K108 | >256 | T248P |
| K109 | >256 | " |
| K110 | 256 | V338L |

The MICs of the resistant mutants ranged from 32 to >256 µg/mL. The editing domains from each of these mutants were sequenced and compared to the wild-type sequence. All resistant colonies had mutations in the LeuRS editing domain (See Tables 4-7), which mapped around the editing domain.

TABLE 7

| | GSK2251052 MIC (mcg/mL) | |
|---|---|---|
| Organism | WT | Mutants |
| E. coli | 1 | 64 → 256 |
| K. pneumoniae | 1 | 256 → 256 |
| P. aeruginosa | 4 | 32 → 256 |

All GSK2251052 Resistant Mutants were Editing Deficient.

The aminoacyl-tRNA synthetase enzyme, LeuRS, ensures the correct amino acid, leucine, is attached to tRNA$^{Leu}$. The LeuRS synthetic active site is capable of aminoacylating tRNA$^{Leu}$ with amino acids structural similar to leucine (norvaline, norleucine, isoleucine and methionine). These mischarged tRNA$^{Leu}$ are hydrolyzed by the editing domain, thus preventing the deleterious incorporation of incorrect amino acids into the growing polypeptide. The laboratory generated mutants were further tested for their ability to grow in defined media with exogenously added amino acids. Norvaline and norleucine, structurally similar to leucine, were tested in M9 minimal media. GSK2251052 resistant mutants from P. aeruginosa ATCC 27853, E. coli ATCC 25922 and K. pneumoniae ATCC 13883 were found to be extremely sensitive to the amino acid norvaline with MICs ranging from 0.25 to 4 µg/mL (Table 8), while wild-type P. aeruginosa, E. coli and K. pneumoniae were resistant, MICs ranging from 16 to >64 µg/mL (Table 8).

TABLE 8

E. coli ATCC 25922, K. pneumoniae ATCC 13883, P. aeruginosa ATCC 27853 wild type and mutants MICs to GSK2251052, norvaline, and norleucine in M9 minimal media

| | MICs in M9 minimal media (µg/mL) | | |
|---|---|---|---|
| Strains | GSK2251052 | Norleucine | Norvaline |
| E. coli ATCC25922 | 1 | 4 | 32 |
| E 101(leuRS Y246H) | 64 | 2 | 4 |
| E 102(leuRS D345G) | >256 | 4 | 0.5 |
| E 107(leuRS G229S) | 128 | 4 | 1 |
| Klebsiella pneumoniae ATCC13883 | 2 | 32 | 16 |
| K 104(leuRS D345Y) | >256 | 16 | 1 |
| K 105(leuRS G229R) | >256 | 32 | 4 |
| K 107(leuRS S227F) | 32 | 64 | 4 |
| K 108(leuRS T248P) | >256 | 64 | 2 |
| K 110(leuRS V338L) | 64 | >64 | 4 |
| P. aeruginosa ATCC27853 | 4 | >64 | >64 |
| P 101 (leuRS T256P) | 128 | >64 | 4 |
| P 106 (leuRS V342M) | >256 | >64 | 0.25 |
| P 108 (leuRS T252P) | >256 | >64 | 0.25 |

This suggested the GSK2251052 resistant mutants are defective in editing and that editing activity is essential for viability in the presence of certain amino acid analogs of leucine.

GSK2251052 resistant mutants were not cross-resistant to commercial antibiotics. E. coli, P. aeruginosa and K. pneumoniae mutants resistant to GSK2251052A were tested for susceptibility to the commercially available antibiotics ciprofloxacin, ceftazidime, chloramphenicol, gentamicin, kanamycin, polymixin B, tobramycin and trimethoprim. GSK2251052 resistant mutants did not have any significant difference in MIC values than wild-type, which suggests that GSK2251052 resistant mutations do not confer cross-resistance to known antibiotics (Tables 9-11).

TABLE 9

E. coli ATCC 25922 wild type and mutants MICs to common antibiotics

| Antibiotics | E. coli ATCC25922 wt. & mutants MICs (µg/mL) | | | |
|---|---|---|---|---|
| | E wt | E 101 | E 102 | E 107 |
| Ciprofloxacin | 0.008 | 0.008 | 0.008 | 0.015 |
| Ceftazadime | 0.5 | 0.5 | 0.5 | 0.5 |
| Chloramphenicol | 8 | 8 | 8 | 8 |
| Gentamicin | 2 | 1 | 1 | 1 |
| Kanamycin | 4 | 4 | 4 | 8 |
| Polymyxin B | 4 | 4 | 4 | 4 |
| Tobramycin | 1 | 1 | 2 | 1 |
| Trimethoprim | 0.5 | 1 | 0.5 | 1 |

TABLE 10

Klebsiella pneumoniae ATCC 13883 wild type and mutants MICs to common antibiotics

| Antibiotics | Klebsiella pneumoniae ATCC13883 wt. and mutants MICs (µg/mL) | | | | | |
|---|---|---|---|---|---|---|
| | K wt. | K 104 | K 105 | K 107 | K 108 | K 110 |
| Ciprofloxacin | 0.125 | 0.03 | 0.06 | 0.06 | 0.03 | 0.03 |
| Ceftazadime | 0.5 | 0.5 | 0.5 | 0.5 | 1 | 0.5 |
| Chloramphenicol | 4 | 8 | 8 | 8 | 8 | 8 |
| Gentamicin | 1 | 1 | 1 | 1 | 0.5 | 1 |
| Kanamycin | 2 | 2 | 2 | 2 | 2 | 1 |
| Polymyxin B | 4 | 8 | 4 | 2 | 4 | 4 |
| Tobramycin | 0.5 | 0.5 | 0.5 | 0.5 | 0.5 | 0.5 |
| Trimethoprim | 1 | 1 | 1 | 1 | 1 | 1 |

TABLE 11

P. aeruginosa ATCC 27853 wild type and mutants MICs to common antibiotics

| Antibiotics | P. aeruginosa ATCC27853 wt. and mutants MICs (µg/mL) | | | |
|---|---|---|---|---|
| | P wt. | P 101 | P106 | P108 |
| Ciprofloxacin | 0.5 | 1 | 1 | 0.5 |
| Ceftazadime | 2 | 4 | 2 | 2 |
| Chloramphenicol | >64 | >64 | >64 | >64 |
| Gentamicin | 8 | 4 | 4 | 4 |
| Kanamycin | >64 | >64 | >64 | >64 |
| Polymyxin B | 4 | 4 | 2 | 4 |
| Tobramycin | 0.5 | 0.5 | 0.5 | 0.5 |
| Trimethoprim | >64 | >64 | >64 | >64 |

This lack of cross-resistance is significantly better than tigecycline. GSK2251052 exhibited a similar resistance frequency to tigecycline in K. pneumoniae, but tigecycline-resistant mutants are multidrug-resistant due to up regulation of an AcrAB efflux pump (Ruzin et al. AAC 2005 49:1017-1022).

Overall, GSK2251052 shows a frequency of resistance of between $10^{-7}$ to $10^{-8}$ against E. coli ATCC 25922, K. pneumoniae ATCC 13883, and P. aeruginosa ATCC 27853 at 24 h and 48 h time points. Moreover, all the resistant mutants showed the following characteristics:

High level resistance to GSK2251052, ranging from 64 to >256 µg/mL

Mutations in the editing domain of leuRS

High sensitivity to norvaline

No cross resistance to common antibiotics

Example 2

Resistant Mutants to GSK2251052 Generated In Vivo

A comparative, dose-ranging study of GSK2251052 vs. imipenem-cilastatin in complicated lower urinary tract infection and pyelonephritis was undertaken with 210 targeted patients (20 actually enrolled) in a phase II clinical trial. The study was designed to determine the appropriate and safe dose for Phase III trials. Doses were 750 mg or 1500 mg twice a day, compared to an active comparator, with an independent safety review committee.

The phase II clinical trial identified four subjects who developed spontaneous resistance to GSK2251052 as evidenced by increased MICs (>32-fold) determined for the clinical isolates from the four subjects. Two of the resistant mutant strains identified were E. coli strains, one was a P. mirabilis strain, and one was a K. pneumoniae strain. The rates of spontaneous resistance for the baseline isolates tested were not significantly different from standard strains previously tested (~$10^{-7}$).

Leucyl-tRNA synthase genes (leuRS) sequenced from the isolates before and following treatment with GSK2251052 show that the resistant isolates contain either single or double editing domain mutations. The E. coli resistant isolates (day 2 onwards) from one patient contain a mutation in the editing domain at position 339 (pro339leu) (see Table 10).

The clinical isolates from the phase II clinical trial described for GSK2251052 were tested for their sensitivity to norvaline, to determine whether the resistant isolates are more sensitive than baseline strains to norvaline.

The E. coli and P. mirabilis strains were cultured on Trypticase Soy Agar/5% blood plates (Becton Dickinson BBL), in cation adjusted Mueller-Hinton II Broth, or in M9 minimal salts (Becton Dickinson) broth containing 0.4% glucose and 200 uM $MgSO_4$. L-Norvaline (Sigma-Aldrich) was prepared at a concentration of 6.4 mg/ml in 100% DMSO, in a final volume of approx 0.5 ml, and stored at −20° C. until required.

Minimum inhibitory concentrations (MICs) were determined using the CLSI (Clinical and Laboratory Standards Institute, formerly NCCLS) recommended broth microdilution methodology [NCCLS, 2003] using defined media. As seen in Table 12, the clinical isolates from subject E. coli 1 showed increased sensitivity to norvaline compared to baseline values (day 1), as evidenced by the decreased MIC values determined at days 2, 3 and 4.

These isolated mutants also showed increased susceptibility to norvaline in M9 minimal media.

TABLE 12

| Subject ID | Visit | GSK2251052 MIC (ug/ml) GSK results | Norvaline MIC (ug/ml) in M9 | LeuRS A.A. Residue Change* |
|---|---|---|---|---|
| E. Coli 1 | day 1 | 0.5 | 4 | NA |
| E. Coli 1 | day 1 | 0.25 | 2 | NA |
| E. Coli 1 | day 2 | 16 | 0.5 | P339L |

TABLE 12-continued

| | | | | |
|---|---|---|---|---|
| E. Coli 1 | day 3 | 16 | 0.5 | P339L |
| E. Coli 1 | day 4 | 16 | 0.5 | P339L |

```
                                              (SEQ ID NO: 1)
LeuS        247         261        331     339     346
E. coli  TTRPDTFMGCTYLAV.........GTGAVMAVPGHDQRDY
           Editing domain 1        Editing domain 2
```

Strains isolated from other subjects that developed resistance to GSK2251052 during the clinical trial did not grow in M9 minimal media, so MICs for norvaline for those strains could not be determined.

Another study was undertaken with *E. coli* parent strain 1161435 and laboratory mutants generated with GSK2251052 from the parent strain, to assess sensitivity of these strains to norvaline and other leucine amino acid analogs. The results of this study are shown in Table 13. As can be seen, the mutants show the most sensitivity to norvaline, but some sensitivity is also observed to L-Norleucine, as evidenced by the decrease in MIC values determined for the mutant strains in M9 minimal media.

TABLE 13

Sensitivity of *Escherichia coli* 1161435 parent and mutant strains B4, B26 and B35 to leucine analogs in Mueller Hinton (MH) and M9 minimal media (M9)

| | 1161435 Parent | | B4 (P339L) | | B26 (R334H) | | B35 (D251N) | |
|---|---|---|---|---|---|---|---|---|
| | MH | M9 | MH | M9 | MH | M9 | MH | M9 |
| L-Norvaline | >128 | >128 | >128 | 2 | >128 | 16 | >128 | 64 |
| L-Isoleucine | >128 | >128 | >128 | >128 | >128 | >128 | >128 | >128 |
| L-Methionine | >128 | >128 | >128 | >128 | >128 | >128 | >128 | >128 |
| L-Valine | >128 | >128 | >128 | >128 | >128 | >128 | >128 | >128 |
| L-Norleucine | >128 | 32 | >128 | 16 | >128 | 8 | >128 | 16 |
| L-Threonine | >128 | >128 | >128 | >128 | >128 | >128 | >128 | >128 |
| 4-Aza-DL-Leucine dihydrochloride | >128 | 64 | >128 | 64 | >128 | 64 | >128 | 32 |
| 5,5,5-Trifluoro-DL-Leucine | >128 | 128 | >128 | 128 | >128 | 64 | >128 | 64 |
| 3-Cyclopentyl-DL-Alanine | >128 | >128 | >128 | >128 | >128 | >128 | >128 | >128 |
| DL-2-Allylglycine | >128 | 16 | >128 | 16 | >128 | 16 | >128 | 32 |
| DL-oxonorvaline | >256 | 128 | >256 | 64 | >256 | 64 | >256 | 128 |
| Levofloxacin | 0.03 | 0.016 | 0.03 | ≤0.008 | 0.03 | 0.03 | 0.03 | 0.016 |

In a second subject, resistant isolates were found to have a Thr247Ile mutation in editing domain 1. At day 6-follow up resistant isolates were found to have two mutations in leuS. Almost all clinical isolates were determined to contain T247I in addition to a second mutation in editing domains 1 or 2. The second mutations include Asp251Asn, Ala323 Val, Arg344Cys/His and Asp345Ala. On Day 11 and at Follow Up a double mutant (R344H; D345A) was also isolated (see Table 14). For these clinical isolates, five independent colonies were characterized from day 6 to late follow-up, and leuS and promoter regions were sequenced from all isolates.

TABLE 14

| Subject ID | Visit | GSK2251052 MIC (ug/ml) GSK results | LeuRS A.A. Residue Change* |
|---|---|---|---|
| E. Coli 2 | day 1 | 0.25 | NA |
| E. Coli 2 | day 2 | 512 | T247I |
| E. Coli 2 | day 3 | 512 | T247I |

TABLE 14-continued

| E. Coli 2 | day 4 | 512 | T247I |
|---|---|---|---|
| E. Coli 2 | day 5 | 512 | T247I |
| E. Coli 2 | day 6 | 1024 | 5x T247I; A323V |
| E. Coli 2 | day 7 | 1024 | 5x T247I; A323V |
| E. Coli 2 | day 8 | 1024 | 5x T247I; A323V |
| E. Coli 2 | day 9 | 1024 | 1x T247I; A323V |
| E. Coli 2 | day 9 | 1024 | 4x T247I; D251N |
| E. Coli 2 | day 10 | 1024 | 2x T247I; D251N |
| E. Coli 2 | day 10 | 1024 | 3x T247I; A323V |
| E. Coli 2 | day 11 | 1024 | 1x T247I; A323V |
| E. Coli 2 | day 11 | 1024 | 4x R344H; D345A |
| E. Coli 2 | day 12 | 1024 | 1x T247I; R344C |
| E. Coli 2 | day 12 | 1024 | 4x T247I; A323V |
| E. Coli 2 | day 13 | 1024 | 5x T247I; D251N |
| E. Coli 2 | End of IV | 1024 | 5x T247I; A323V |
| E. Coli 2 | Follow-up | 1024 | 5x R344H; D345A |

```
                                                  (SEQ ID NO: 1)
LeuS       247 251       261     323      331      344345346
E. coli  TTRPDTFMGCTYLAV...A....GTGAVMAVPGHDQRDY
            Editing domain 1         Editing domain 2
```

Threonine247 is located in a threonine-rich conserved region in *E. coli* LeuRS ($T_{247}TRPDT_{252}$) in the CP1 (connective polypeptide 1) domain of LeuRS important for editing function (R. S. Mursinna et al. "A Conserved Threonine Within *Escherichia coli* Leucyl-tRNA Synthetase Prevents Hydrolytic Editing of Leucyl-tRNA$^{Leu}$", *Biochemistry*, 2001, 40 (18), pp 5376-5381). Thr247 stabilizes the transition state in the catalytic editing reaction of LeuRS, and it directly interacts with the benzoxaborole adduct that forms between GSK2251052 and the tRNA$^{Leu}$. However, T247A mutants were shown to have Leucylation capabilities similar to those of wild type LeuRS, and Leu-tRNA$^{Leu}$ was hydrolyzed at low levels in this mutant, similar to the hydrolysis rates of wild type LeuRS (See pp. 5377-5378 and FIG. 2 of R. S. Mursinna et al., *Biochemistry*, 2001, 40). Unlike the T247A mutants studied by Mursinna et al., the T247I mutation in the clinical isolate mutants of LeuRS that arose in response to treatment with GSK2251052 surprisingly impacts the binding of GSK2251052 to the editing domain of LeuRS directly. It is postulated that the other mutations observed in the clinical isolates (Pro339Leu in subject *E. coli* 1, and Asp251Asn, Ala323 Val, Arg344Cys/His and Asp345Ala in subject *E. coli* 2) narrow the binding pocket in the editing domain of *E. coli* LeuRS, further impacting the ability of GSK2251052 to bind to LeuRS.

An additional study which sequenced a range of laboratory generated GSK2251052 resistant mutants revealed 45 individual mutations at 22 different amino acid positions within the LeuRS editing domain. Several of these amino acid positions correlated with or were identical to mutated positions in the non-susceptible clinical isolates from the phase II clinical trial.

Example 3

Measurement of the Suppression of the Emergence of a Resistant Bacterial Strain In Vitro Clinical strains of *Escherichia coli* and *Proteus mirabilis* isolated from the above-described clinical trial study (Table 12), along with other *E. coli* strains were used to measure the suppression of the emergence of resistant bacterial strains in vitro and to determine the susceptibility of these GSK2251052 resistant bacterial isolates to norvaline. Increased sensitivity to this leucine analog would suggest an editing domain mutation in LeuRS. Moreover, in order to find out if sub-inhibitory concentrations of norvaline could suppress growth of GSK2251052 resistant mutants under restricted amino acid conditions in the laboratory, the frequency of spontaneous resistance to GSK2251052 was determined for *Escherichia coli* 1162222 (standard strain) and the *E. coli* isolate (baseline strain from subject *E. coli* 1, isolated from blood in the above-described clinical study in Example 2) in the presence of norvaline in minimal media.

Throughout this study *E. coli* and *P. mirabilis* strains were cultured on Trypticase Soy Agar/5% blood plates, on M9 salts/1.2% Bacto Agar plates, in Cation Adjusted Mueller-Hinton II Broth (CAMHB), or in M9 Minimal Salt Broth containing 0.4% glucose and 200 µM MgSO$_4$. GSK2251052 and norvaline were prepared at a concentration of 6.4 mg/mL (free base) in 100% DMSO and 100% water respectively, aliquoted in 0.5 mL individual stocks, and stored at −20° C. until required.

Minimum inhibitory concentrations (MICs) were determined for each organism using the CLSI (Clinical and Laboratory Standards Institute) recommended broth microdilution methodology [CLSI, 2009].

The effective inhibitory concentration of bacterial growth in plates under the conditions of the frequency of resistance study was determined for certain organisms by plating 2-fold dilution series of compound of interest onto the appropriate agar plates.

Preparation of Plates

An appropriate amount of a 6.4 mg/mL compound stock was added to appropriate broth media to give a final volume of 1 mL. This pre-warmed solution was then added to 19 mL molten agar at 50° C. to yield 20 mL of agar at appropriate multiples of the MIC of each organism/compound combination. Plates were poured and left to cool and solidify.

Preparation of Inoculum

Cultures were prepared by inoculating broth with a bacterial suspension in saline, prepared from plates derived from individual colonies. For each organism, 100 mL of CAMHB was inoculated with 5 mL of a bacterial suspension with turbidity equivalent to 0.5 McFarland. These cultures were incubated on an orbital shaker at 37° C. until the broth was visibly turbid (approximately 3 hours). Following incubation, cultures were centrifuged at 11,000 g for 10 min at 4° C. The culture media was then decanted and cell pellets were resuspended to an appropriate cell concentration in fresh CAMHB or M9. The ratio of OD$_{625}$ to CFU/mL used to approximate culture size is 0.1:1.0×10$^8$. Targeted *E. coli* cell concentrations were 2×10$^9$ CFU/mL.

Plating

Viable counts were performed to determine the concentration of the initial test inoculum using the following steps: 1) ten-fold serial dilutions of each sample were prepared; 2) three 20 µL aliquots from wells corresponding to 10$^{-5}$, 10$^{-6}$, 10$^{-7}$ and 10$^{-8}$ dilutions were plated onto the appropriate agar plates; 3) the plates were incubated overnight at 35° C. and counts were performed at the dilution that provided distinguishable colonies; 4) an average of the three aliquots was used to determine the number of colony forming units (CFU) in the original sample.

In addition, 100 µL of each cell suspension was spread onto the surface of plates containing the appropriate multiple of MIC concentration of compound and a control agar plate containing no compound. Plates were incubated at 35° C. in ambient air.

Reading Plates and Confirming Resistance

Colonies were counted after 24, 48 and 72 hours. Colony size was noted, and a representative set of colonies was frozen in media containing 12.5% glycerol. In order to confirm their resistance phenotype, the susceptibility of these isolates to the selecting agent was tested by broth microdilution methodology.

Drugs and Materials

GSK2251052 batch number 2251052-B-5(W)-01P, 85% purity, was obtained from GlaxoSmithKline in Upper Providence, Pa., USA.

Cation Adjusted Mueller Hinton II Broth was obtained from the GSK Media Prep Laboratory at Upper Merion, Pa., USA.

Trypticase Soy Agar with 5% sheep blood plates (catalog #221261) were obtained from BD BBL, NJ, USA.

M9 Minimal Salt Broth was made up according to manufacturers recommendations with M9 Minimal Salts 5× (catalog #248510) obtained from Becton Dickinson, Md., USA.

L-Norvaline (catalog # N7627-1G) was obtained from Sigma-Aldridge, USA.

Bacto Agar was obtained from BD Difco, N.J., USA.

Data Analysis

The frequency of spontaneous resistance was calculated by dividing the total number of resistant colonies growing on plates containing antibiotic by the total number of colony forming units plated. In order to confirm the resistance phenotype, the MIC of the selecting agent was determined against a representative number of colonies from each antibiotic concentration/strain combination. Colonies were defined as resistant if their MIC was ≥4-fold the MIC of the wild-type strain. The total number of resistant colonies on the plates was extrapolated from the representative set tested.

Results
Determination of MIC in M9 Minimal Media

Strains tested are detailed in Table 15. MICs for norvaline and GSK2251052 could only be determined for *E. coli* isolates from subject *E. coli* 1 (Table 16) as M9 Minimal Media could not sustain growth of *E. coli* isolates from subject *E. coli* 2 (isolates 2a-2o) or *P. mirabilis* isolates (isolates 3a-3c) from subject *E. coli* 3. *E. coli* strains isolated from subject *E. coli* 1's blood on Days 2, 3 and 4 of this study (isolates 1c, 1d and 1e) showed increased susceptibility to norvaline with respect to baseline cultures isolated from blood (isolate 1a) or urine (isolate 1b) from subject *E. coli* 1 on Day 1, with MICs decreasing from 4 or 2 µg/mL to 0.5 µg/mL (Table 16). This phenotype is consistent with a mutation in the editing site of LeuRS, which could also be responsible for the concomitant decrease in susceptibility to GSK2251052 observed in isolates from Days 2, 3 and 4 (Table 16).

TABLE 15

Identification number and source of bacterial strains used in this study

| Subject ID | Source | Visit | Strain Number | Isolate |
|---|---|---|---|---|
| *E. coli* 1 | Blood | Day 1 | Isolate 1a | *E. coli* |
| *E. coli* 1 | Urine | Day 1 | Isolate 1b | *E. coli* |
| *E. coli* 1 | Blood | Day 2 | Isolate 1c | *E. coli* |
| *E. coli* 1 | Blood | Day 3 | Isolate 1d | *E. coli* |
| *E. coli* 1 | Blood | Day 4 | Isolate 1e | *E. coli* |
| *E. coli* 2 | Urine | Day 1 | Isolate 2a | *E. coli* |
| *E. coli* 2 | Urine | Day 2 | Isolate 2b | *E. coli* |
| *E. coli* 2 | Urine | Day 3 | Isolate 2c | *E. coli* |
| *E. coli* 2 | Urine | Day 4 | Isolate 2d | *E. coli* |
| *E. coli* 2 | Urine | Day 5 | Isolate 2e | *E. coli* |
| *E. coli* 2 | Urine | Day 6 | Isolate 2f | *E. coli* |
| *E. coli* 2 | Urine | Day 7 | Isolate 2g | *E. coli* |
| *E. coli* 2 | Urine | Day 8 | Isolate 2h | *E. coli* |
| *E. coli* 2 | Urine | Day 9 | Isolate 2i | *E. coli* |
| *E. coli* 2 | Urine | Day 10 | Isolate 2j | *E. coli* |
| *E. coli* 2 | Urine | Day 11 | Isolate 2k | *E. coli* |
| *E. coli* 2 | Urine | Day 12 | Isolate 2l | *E. coli* |
| *E. coli* 2 | Urine | Day 13 | Isolate 2m | *E. coli* |
| *E. coli* 2 | Urine | End of IV TX | Isolate 2n | *E. coli* |
| *P. mirabilis* 1 | Urine | Day 1 | Isolate 3a | *P. mirabilis* |
| *P. mirabilis* 1 | Urine | Day 2 | Isolate 3b | *P. mirabilis* |
| *P. mirabilis* 1 | Urine | End of IV TX | Isolate 3c | *P. mirabilis* |

TABLE 16

Minimal Inhibitory Concentration (MIC) Values for GSK2251052 and Norvaline in M9 Minimal Media against *E. coli* isolates from subject *E. coli* 1

| | | | | Mic (µg/mL) | |
|---|---|---|---|---|---|
| Subject ID | Source | Visit | Isolate | GSK2251052 | Norvaline |
| *E. coli* 1 | Blood | Day 1 | Isolate 1a | 1 | 4 |
| *E. coli* 1 | Urine | Day 1 | Isolate 1b | 1 | 2 |
| *E. coli* 1 | Blood | Day 2 | Isolate 1c | 32 | 0.5 |
| *E. coli* 1 | Blood | Day 3 | Isolate 1d | 32 | 0.5 |
| *E. coli* 1 | Blood | Day 4 | Isolate 1e | 32 | 0.5 |

Frequency of Resistance Studies

The frequency of spontaneous resistance to GSK2251052 in the presence of norvaline was determined for *E. coli* 1162222 (standard strain) and clinical isolate 1a of *E. coli* (baseline strain from subject *E. coli* 1) grown in M9 Minimal Media.

Preliminary studies had shown that while GSK2251052 inhibited *E. coli* growth on plates at a similar concentration than in broth, norvaline had a much weaker antibacterial activity in agar plates and a bacterial lawn could still be observed in the presence of 64 µg/mL of norvaline, although the density of the background growth decreased with increasing concentrations of this leucine analog. Given this result, the study was performed in M9 salt/1.2% bacto agar plates with a fixed concentration of GSK2251052 of 4 µg/mL (corresponding to 4×MIC) and 2-fold serial dilutions of norvaline starting at a top concentration of 64 µg/mL.

The number of spontaneous mutants resistant to GSK2251052 decreased with increasing concentrations of norvaline for both the *E. coli* baseline strain and *E. coli* clinical isolate 1a from subject *E. coli* 1 in minimal media (Table 17). In the absence of norvaline, the frequency of resistance to GSK2251052 was $4.9 \times 10^{-8}$ for the baseline *E. coli* strain. Addition of norvaline at 8 µg/mL reduced the appearance of mutants by 10-fold. The frequency of resistance decreased even further to $<1 \times 10^{-9}$ in the presence of concentrations of norvaline ≥32 µg/mL (Table 17). Similarly, the frequency of resistance to GSK2251052 in *E. coli* clinical isolate 1a from subject *E. coli* 1 decreased from $3.8 \times 10^{-7}$ in the absence of norvaline to $4.8 \times 10^{-8}$ with the addition of 2 µg/mL and to $<1.7 \times 10^{-9}$ with concentrations of norvaline of ≥4 µg/mL (Table 17).

TABLE 17

Effect of Norvaline in the Frequency of Spontaneous Resistance to GSK2251052 at 4 µg/mL for Two *E. coli* Strains Grown in Minimal Media or in Rich Media

| | Frequency of Resistant to GSK2251052 (4 µg/mL) | | | |
|---|---|---|---|---|
| | M9 Agar | | CAMH Agar | |
| Norvaline (µg/mL) | *E. coli* baseline strain | *E. collie* Isolate 1a | *E. coli* baseline strain | *E. coli* Isolate 1a |
| 0 | $4.9 \times 10^{-8}$ | $3.8 \times 10^{-7}$ | $1.2 \times 10^{-7}$ | $6.3 \times 10^{-8}$ |
| 2 | $2.8 \times 10^{-8}$ | $4.8 \times 10^{-8}$ | $5.0 \times 10^{-8}$ | $7.6 \times 10^{-8}$ |
| 4 | $2.0 \times 10^{-8}$ | $<1.7 \times 10^{-9}$ | $1.2 \times 10^{-7}$ | $4.7 \times 10^{-8}$ |
| 8 | $6.0 \times 10^{-8}$ | $<1.7 \times 10^{-9}$ | $6.8 \times 10^{-8}$ | $6.3 \times 10^{-8}$ |
| 16 | $3.0 \times 10^{-9}$ | $<1.7 \times 10^{-9}$ | $6.1 \times 10^{-8}$ | $4.5 \times 10^{-8}$ |
| 32 | $<1.0 \times 10^{-9}$ | $<1.7 \times 10^{-9}$ | $1.1 \times 10^{-7}$ | $5.0 \times 10^{-8}$ |
| 64 | $<1.0 \times 10^{-9}$ | $<1.7 \times 10^{-9}$ | $9.3 \times 10^{-8}$ | $5.3 \times 10^{-8}$ |

A similar study was performed with both *E. coli* strains (baseline strain and clinical isolate from subject *E. coli* 1) plated on rich media in the presence of GSK2251052 at 4 µg/mL and variable concentrations of norvaline. Under these conditions, the frequency of resistance to GSK2251052 remained the same regardless of the concentration of norvaline present on the plates (Table 17).

Day 2, Day 3 and Day 4 blood culture *E. coli* isolates from subject *E. coli* 1 of the study are more susceptible to norvaline than the baseline (Day 1) blood or urine culture isolates (isolates 1a and 1b) from this subject. When tested in minimal media, norvaline MICs decrease from 4 or 2 µg/mL to 0.5 µg/mL. This phenotype is consistent with an editing site mutation in LeuRS, likely responsible for the decreased susceptibility to GSK2251052 observed in this case.

Spontaneous frequency of resistance studies show that norvaline, at concentrations that do not inhibit growth of *E. coli* (baseline strain) or *E. coli* clinical isolate 1a (from subject *E. coli* 1) on M9 minimal media plates, clearly suppresses the appearance of GSK2251052 resistant mutants from these strains. There is an approximately 50-fold or greater decrease in the frequency of resistance to GSK2251052 in *E. coli* (baseline strain), from $4.9 \times 10^{-8}$ in the absence of norvaline to $<1 \times 10^{-9}$ in the presence of >32 μg/mL. Possibly even more substantial is the reduction observed in the *E. coli* clinical isolate from subject *E. coli* 1, where frequency of spontaneous resistance decreases over 200-fold from $3.8 \times 10^{-7}$ in the absence of this leucine analog to $<1.7 \times 10^{-9}$ with concentrations of norvaline >4 μg/mL. Clearly, *E. coli* mutants resistant to GSK2251052 are more susceptible to norvaline than their parent strains suggesting the presence of mutations in the editing domain of LeuRS. In a similar study in rich media the presence of norvaline did not change the frequency of spontaneous resistance in either of these two strains at concentrations up to 64 μg/mL, as expected given that the abundance of leucine in the media would prevent significant binding of norvaline to LeuRS.

Any bacterial mutants identified will be sequenced to determine the location of individual mutations and which amino acid position(s) within the LeuRS has been changed, and whether the mutations occur in the editing domain of LeuRS. Any mutations found will then be further assessed to determine whether the amino acid mutation positions correlate with key positions in the editing domain of LeuRS known to be important in editing function to aid in understanding the role of the mutations in increased sensitivity by the bacterial mutants to norvaline and/or other amino acids.

It is to be understood that the invention covers all combinations of aspects with all other suitable aspects and/or exemplary embodiments described herein. It is to be understood that the invention also covers all combinations of exemplary embodiments with all other suitable aspects and/or exemplary embodiments described herein.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes Statement to Support Sequence Listing This submission is accompanied by a computer readable form containing SEQ ID NO. 1. The sequence listing in computer readable form was prepared through the use of the software program "PatentIn, version 3.5" in accordance with 37 C.F.R. §§1.821-1.825.

According to the Legal Framework for EFS-Web (September 2008), if a sequence listing text file submitted via EFS-Web complies with the requirements of 37 C.F.R. §1.824(a)(2)-(6) and (b), the text file will serve as both the paper copy required by 37 C.F.R. §1.821(c) and the CRF required by 37 C.F.R. §1.821(e). Therefore, a paper copy of the referenced sequence listing is not included with this application.

What is claimed is:

1. A combination of an amino acid or amino acid salt and a compound having a structure according to formula II:

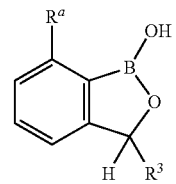

II wherein $R^3$ is a member selected from H, cyano, substituted or unsubstituted nitroalkyl and substituted or unsubstituted aminoalkyl; $R^a$ is a member selected from H and —$YR^5$;

wherein Y is a member selected from O and S; $R^5$ is a member selected from H, substituted or unsubstituted alkyl and substituted or unsubstituted heteroalkyl with the proviso that $R^a$ and $R^3$ cannot both be H; and with the proviso that when $R^3$ is H, $R^a$ does not have a structure which is a member selected from: unsubstituted benzyloxy, —OCH$_2$COOH, methoxy, ethoxy, with the proviso that when $R^a$ is H, $R^3$ is not cyano, or a salt thereof wherein the amino acid or amino acid salt is selected from the group consisting of allylglycine, norvaline, methionine, norleucine, isoleucine, homocysteine, homoserine, and valine.

2. A combination of an amino acid or amino acid salt and a compound having a structure according to formula III:

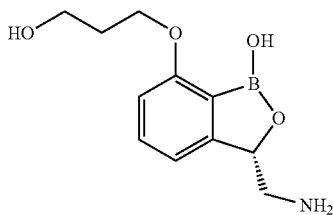

wherein the amino acid or amino acid salt is selected from the group consisting of allylglycine, norvaline, methionine, norleucine, isoleucine, homocysteine, homoserine, and valine.

3. A combination according to claim 2, wherein the compound is a compound of formula III and the amino acid or its salt is norvaline.

4. A method for decreasing the frequency of resistance and/or reducing the rate of resistance and/or suppressing the emergence of resistance that develops in bacteria exposed to a substituted benzoxaborole or salt thereof, comprising:
administering to a subject having a bacterial infection a combination of a substituted compound of formula II or salt thereof and an amino acid or a salt thereof, wherein the amino acid or salt thereof is selected from the group consisting of allylglycine, norvaline, methionine, norleucine, isoleucine, homocysteine, homoserine, and valine.

5. A method for decreasing the frequency of resistance and/or reducing the rate of resistance and/or suppressing the emergence of resistance that develops in bacteria exposed to a substituted benzoxaborole or salt thereof, comprising:
administering to a subject having a bacterial infection a combination of a substituted compound of formula III or salt thereof and an amino acid or a salt thereof, wherein the amino acid or salt thereof is selected from the group consisting of allylglycine, norvaline, methionine, norleucine, isoleucine, homocysteine, homoserine, and valine.

6. A method for treating a bacterial infection in a subject, comprising administering to the subject a combination according to claim 2.

7. A method for treating a bacterial infection in a subject, comprising administering to the subject a combination according to claim 4.

* * * * *